United States Patent [19]

Hammarskjöld et al.

[11] Patent Number: 5,585,263
[45] Date of Patent: Dec. 17, 1996

[54] PURIFIED RETROVIRAL CONSTITUTIVE TRANSPORT ENHANCER AND ITS USE TO FACILITATE MRNA TRANSPORT, AND TO PRODUCE RECOMBINANT, ATTENUATED HIV

[75] Inventors: Marie-Louise Hammarskjöld; David Rekosh, both of Earlysville; Molly Bray, Charlottesville, all of Va.; Eric Hunter, Birmingham, Ala.

[73] Assignees: University of Alabama at Birmingham Research Foundation, Birmingham, Ala.; Research Foundation of State University of New York, Amherst, N.Y.

[21] Appl. No.: 246,987

[22] Filed: May 20, 1994

[51] Int. Cl.$^6$ .............................. C12N 7/04; C12N 15/00; C07H 21/04; A61K 39/21
[52] U.S. Cl. .................... 435/236; 536/24.1; 424/207.1; 424/208.1; 435/172.3
[58] Field of Search .............................. 435/5, 7.21, 172, 435/236, 172.3; 536/24.1; 424/207.1, 208.1

[56] References Cited

PUBLICATIONS

Bray et al., "A Small Element from the Mason–Pfizer Monkey Virus Genome Makes Human Immunodeficiency Virus Type 1 Expression and Replication Rev–Independent", *Proc. Natl. Acad. Sci. USA*, vol. 91, Feb. 1994, pp. 1256–1260.

Osborne and Silver, 1993, "Nucleocytoplasmic transport in the yeast *Saccharomyces cerevisiae*", Annu. Rev. Biochem. 62:219–254.

Kadowaki et al., 1992, "A conditional yeast mutant deficient in mRNA transport from nucleus to cytoplasm", Proc, Natl. Acad. Sci. USA 89:2312–2316.

Del Pozzo et al., 1994, "Control of nucleo–cytoplasmic HLA–DRA mRNA partitioning by interaction of a retention signal with compartmentalized proteins", J. Mol. Biol. 240:193–204.

Alonso–Caplen et al., 1992, "Nucleocytoplasmic transport: the influenza virus NS1 protein regulates the transport of spliced NS2 mRNA and its precursor NS1 mRNA", Genes Devel. 6:255–267.

Latchman, D., 1990, "Cell–type-specific splicing factors and the regulation of alternative RNA splicing", New Biol. 2:297–303.

Gomeza et al., 1994, "Cellular distribution and regulation by cAMP of the GABA transporter (GAT–1) mRNA", Molec. Brain Res. 21:150–156.

*Primary Examiner*—Robert D. Budens
*Assistant Examiner*—Jeffrey S. Parkin
*Attorney, Agent, or Firm*—Hodgson, Russ, Andrews, Woods & Goodyear

[57] ABSTRACT

A novel retroviral nucleotide sequence comprising a constitutive transport enhancer which functions to transport mRNA transcripts from the nucleus to the cytoplasm of a cell, wherein the mRNA transcript is either differentially spliced, alternatively spliced, incompletely spliced, or unspliced. Also disclosed is a recombinant attenuated HIV containing only structural proteins gag, pol, and env, wherein the expression of the structural proteins is rev-independent and facilitated by the constitutive transport enhancer.

5 Claims, 13 Drawing Sheets

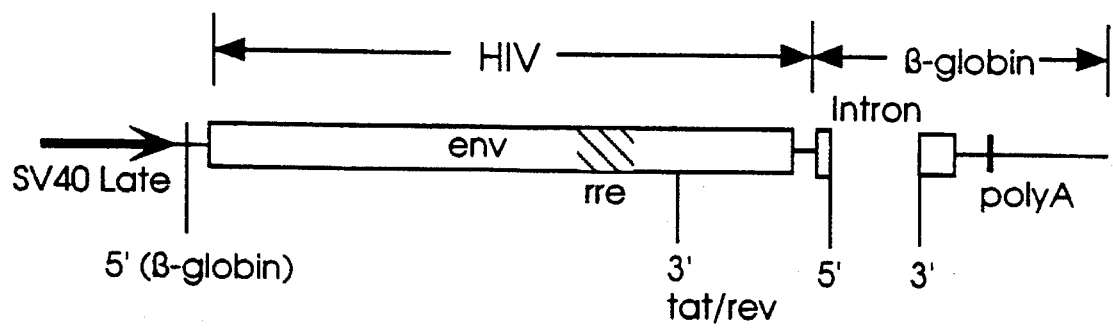
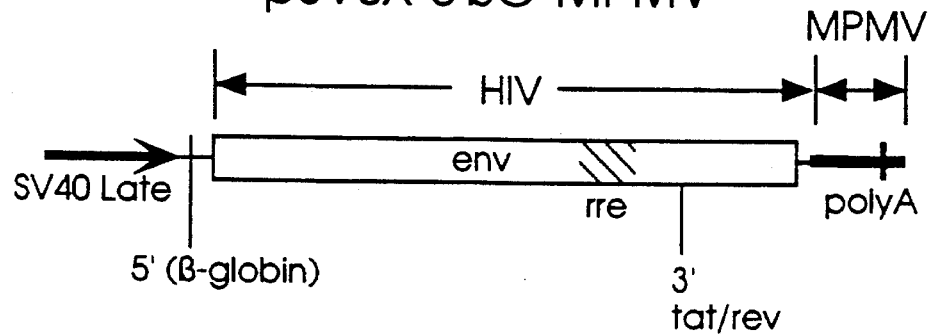
FIG. 1

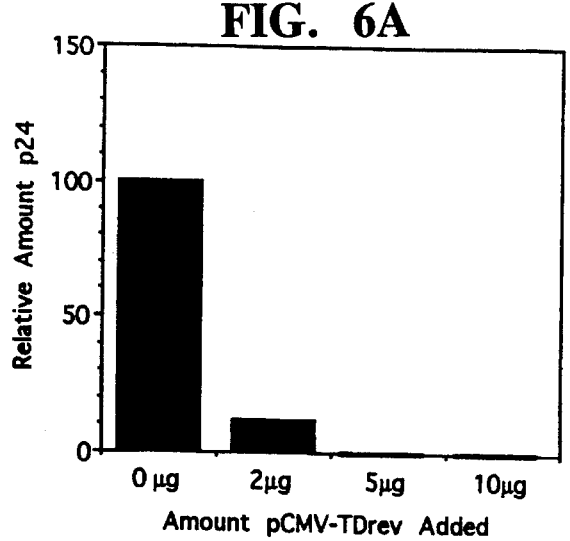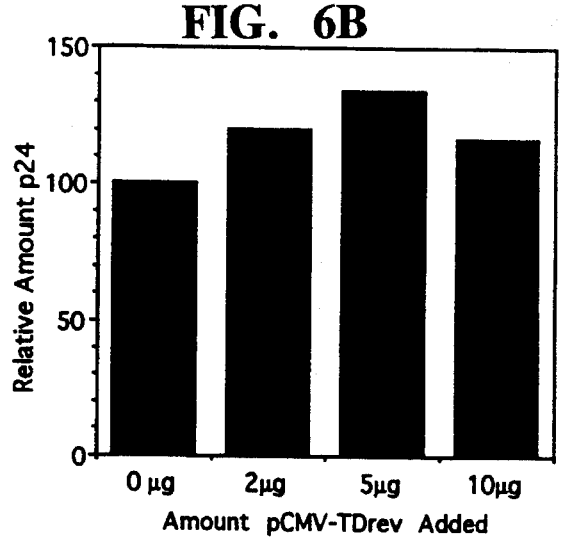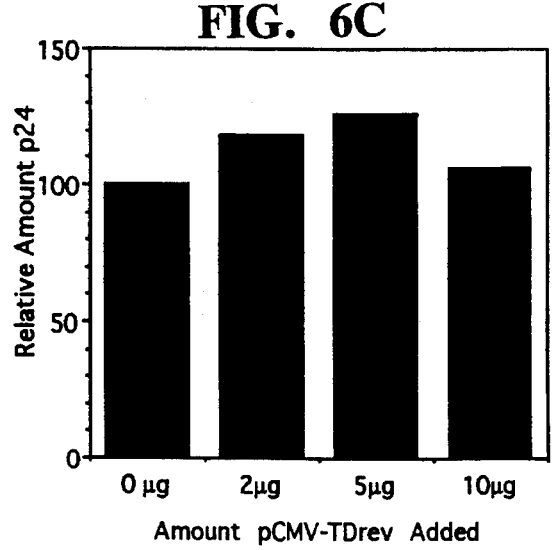

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

(A) LENGTH: 219 nucleotides
(B) TYPE: nucleic acid
(C) STRANDEDNESS: single-stranded
(D) TOPOLOGY: linear (ii) ORIGINAL SOURCE:
(A) ORGANISM: Mason-Pfizer monkey virus (iii) FEATURE:
(A) LOCATION: GenBank file SIVMPCG (iv) PUBLICATION INFORMATION:
(A) AUTHORS: Soniga, Pierre; Barker, Christopher; Hunter, Eric; and Wain-Hobson, Simon
(B) TITLE: Nucleotide Sequence of Mason-Pfizer Monkey Virus
(C) JOURNAL: Cell
(D) VOLUME: 45
(E) PAGES: 375-385
(F) DATE: May 9, 1986

(v) SEQUENCE DESCRIPTION: SEQ ID NO:1:

```
AGACTGGACA  GCCAATGACG  GGTAAGAGAG  TGACATTTCT  CACTAACCTA   50

AGACAGGAGG  GCCGTCAAAG  CTACTGCCTA  ATCCAATGAC  GGGTAATAGT  100

GACAAGAAAT  GTATCACTCC  AACCTAAGAC  AGGCGCAGCC  TCCGAGGGAT  150

GTGTCTTTTG  TTTTTTATAA  TTAAAAAGGG  TGACATGTCC  GGAGCCGTGC  200

TGCCCGGATG  ATGTCTTGG       219
```

(2) INFORMATION FOR SEQ ID NO:2:

(i) SEQUENCE CHARACTERISTICS:
(A) LENGTH: 154 nucleotides
(B) TYPE: nucleic acid
(C) STRANDEDNESS: single-stranded
(D) TOPOLOGY: linear (ii) ORIGINAL SOURCE:
(A) ORGANISM: Mason-Pfizer monkey virus (iii) FEATURE:
(A) LOCATION: GenBank file SIVMPCG (iv) PUBLICATION INFORMATION:
(A) AUTHORS: Soniga, Pierre; Barker, Christopher; Hunter, Eric; and Wain-Hobson, Simon
(B) TITLE: Nucleotide Sequence of Mason-Pfizer Monkey Virus
(C) JOURNAL: Cell
(D) VOLUME: 45
(E) PAGES: 375-385
(F) DATE: May 9, 1986

(v) SEQUENCE DESCRIPTION: SEQ ID NO:2:

```
AGACTGGACA  GCCAATGACG  GGTAAGAGAG  TGACATTTCT  CACTAACCTA   50

AGACAGGAGG  GCCGTCAAAG  CTACTGCCTA  ATCCAATGAC  GGGTAATAGT  100

GACAAGAAAT  GTATCACTCC  AACCTAAGAC  AGGCGCAGCC  TCCGAGGGAT  150

GTGT   154
```

PURIFIED RETROVIRAL CONSTITUTIVE TRANSPORT ENHANCER AND ITS USE TO FACILITATE MRNA TRANSPORT, AND TO PRODUCE RECOMBINANT, ATTENUATED HIV

This invention was made with government support under grant numbers AI-25721 and AI-25784, awarded by the National Cooperative Drug Discovery Group; and grant numbers AI-27290, AI-30399, and AI-33319, awarded by the National Institutes of Allergy and Infectious Disease. The government has certain rights in this invention.

1. BACKGROUND OF THE INVENTION

1.1 Field of the Invention

The present invention relates to complex retroviral protein expression and viral replication independent of the expression of a viral transacting protein such as rev, rex, or functionally equivalent protein. More particularly, this invention provides for the rev-independent expression of HIV gag/pol, env, vif, vpr, and vpu proteins by introducing into the host cells a vector/virus containing the nucleic acid sequence encoding HIV protein(s), and a genetic enhancer that promotes the transport of intron-containing mRNA. Also, this invention provides for cytoplasmic expression of cellular sequences, containing introns, which normally do not exit the nucleus.

1.2 Description of the Background and Related Art
A. Splicing of HIV RNA

The human immunodeficiency virus (HIV) is a lymphotropic retrovirus implicated in the pathogenesis of AIDS. As compared to other characterized retroviruses, the HIV genome appears to contain at least six novel genes (vif, vpr, tat, rev, vpu, and nef). However, a common feature of all replication-competent retroviruses is that the primary transcription product from the proviral DNA contains at least three open reading frames gag, pol and env, positioned 5' to 3' in the RNA. This product is always a genome length RNA that is spliced to generate subgenomic species, wherein the spliced RNA function as mRNA for env or other proteins that are sometimes encoded near the 3' end of the genome. Splicing, the removal of intervening sequences, is a multistep process requiring the participation of small nuclear RNAs and protein factors that together make up small nuclear ribonucleoprotein particles (snRNP) which in turn form a large complex termed the spliceosome.

In the case of the "simple" Oncornavirus subfamily of retroviruses, a single 5' splice site is positioned near the 5' end of the primary transcript and splicing involves the use of one or two 3' acceptor sites positioned downstream in the RNA. Thus, the subgenomic molecules are always singly spliced and have had most or all of the coding region for gag and pol removed. In these RNAs, the gag and pol region has been defined as an intron. However, because splicing is inefficient, enough full length RNA remains to function as both the mRNA for the gag and pol genes and as the molecule that is packaged into virus particles (Coffin, 1991, in *Fundamental Virology*, eds. Field et al., pp.645–708, Raven Press Ltd.).

The situation in HIV, a member of the Lentivirus subfamily of retroviruses, is more complex. In this case, the coding regions of several novel genes are positioned near the center of the primary transcript between gag-pol and env and at the 3' end of the genome (Wong-Staal, 1991, in *Fundamental Virology*, eds. Field et al., pp.709–723, Raven Press Ltd.). The central region of the genome also contains several 5' and 3' splice sites, which, in conjunction with the conventionally positioned 5' splice site near the 5' end of the RNA, are used for differential splicing of the primary transcript into over twenty different species of mRNA (Schwartz et al., 1990, J. Virol. 64:2519–2529; Schwartz et al., 1990, J. Virol. 64:5448–5456; Schwartz et al., 1991, Virology 183:677–686). These RNAs are either singly or multiply spliced. A consequence of this complicated splicing scheme is that env, as well as gag-pol, has been defined as an intron in the multiply spliced mRNAs.

B. The Relationship Between Rev, Splicing and HIV Gene Expression and Replication In most cases, cellular mRNAs contain introns that are removed by splicing before transport to the cytoplasm occurs. Transport to the cytoplasm is required for the mRNA to interact with the ribosomes and accessory factors in the process of protein synthesis. Recent studies have suggested that intron-containing RNAs are usually prevented from exiting the nucleus due to the binding of splicing factors (Chang and Sharp, 1989, Cell 59:789–795; Legrain and Rosbash, 1989, Cell 57:573–583); although there are a few examples of differentially spliced cellular transcripts that are transported with a retained intron (McKeown, 1992, Annual Rev. of Cell Biol. 8:133–155). Little is known about the mechanisms that allow these mRNAs to be transported.

The rev gene has been shown to be essential for the production of virus (herein "rev" refers to the gene and "rev" refers to the gene product; this convention is also followed for other gene/protein pairs such as env/env, etc.). Using infectious proviral clones of HIV to study rev function, it has been demonstrated that mutations in this gene led to severely reduced levels of protein from gag and env (Feinberg et al., 1986, Cell 46:807–817; Sodroski et al., 1986 Nature 321:412–417). In these studies, in the absence of rev, the levels of large mRNAs encoding the structural proteins were reduced, whereas the levels of doubly spliced small RNAs encoding nonstructural proteins were increased. Similarly, using an envelope protein expression vector system, when rev was deleted from the vector, steady-state levels of env mRNA in the cytoplasm were greatly reduced; env RNA accumulated in the nucleus; and no env protein could be detected unless rev was provided in trans (Hammarskjöld et al., 1989, J. Virol. 63:1959–1966).

It has been shown that the HIV rev protein functions to specifically allow nuclear export of unspliced and singly spliced HIV RNA (Emerman et al., 1989, Cell 57:1155–1165; Felber et al., 1989, Proc. Natl. Acad. Sci. USA 86:1496–1499; Hammarskjöld et al., 1989, supra; Malim et al., 1989, Nature 338:254–257). These RNAs contain complete introns and are retained in the nucleus in the absence of rev. The details of how rev functions are not known, although it is clear that rev action requires it to bind to a specific element in the HIV RNA known as the rev responsive element (RRE) (Daly et al., 1989 Nature 342:816–819; Hammarskjöld et al., 1989, supra; Zapp and Green, 1989, Nature 342:714–716).

Another subfamily of complex Retroviruses, typified by HTLV I and II, seems to have evolved a mechanism similar to HIV to facilitate the transport of intron-containing RNA. These viruses utilize a protein called rex, which, like rev, must bind to a specific element present in the viral RNA (RXRE) (Ahmed et al., 1990, Genes Dev. 4:1014–1022). Rex has also been shown to substitute for rev in promoting the transport of rev-dependent mRNA (Rimsky et al., 1988, Nature 335:738–740; Lewis et al., 1990, J. Virol. 64:1690–1697). While the complex retroviruses have developed rev and rex regulation to allow the cytoplasmic expression of their intron-containing RNA, the simple retroviruses appear not to have similar transacting proteins.

C. Relevance to Therapy against AIDS

An important aspect in identifying anti-viral compounds that are effective against HIV is the development of in vitro assays that can be used to screen for agents that selectively interfere with the different processes involved in HIV infection and replication. One such assay, described in U.S. Pat. No. 4,910,132 involves a virus-free assay that tests the ability of compounds to inhibit specifically the synthesis of the HIV gp120 envelope protein. Another assay using recombinant vectors was developed to detect agents that would inhibit fusion between env producing cells and CD4+ cells (Nelson et al.; 1989, Vth International AIDS Conference, Montreal, Quebec, Canada). However, these assays employed env-producing vectors that also encoded rev, because, inter alia, rev is required for env synthesis. Thus, in vitro assays such as these aren't able to distinguish between compounds acting to inhibit processes involving gp 120 from compounds affecting rev activity. Similarly, in vitro assays, using subgenomic constructs for the production of gag or gag-pol, aren't able to distinguish between compounds acting to inhibit processes involving these proteins from compounds affecting rev activity.

Much research has been focused on the development of a vaccine against AIDS, particularly a vaccine that can readily elicit significant levels of neutralizing antibodies that would prevent the debilitating effects of HIV infection. Vaccine candidates include inactivated virus (see for example, Gibbs et al., 1991, Proc. Natl. Acad. Sci. USA 88:3348–52), virus-like particles (Smith et al., 1990, J. Virol. 64:2743–2750), gag/env protein (U.S. Pat. No. 4,925,784), recombinant fusion polypeptides containing HIV envelope protein or portions thereof (U.S. Pat. No. 5,130,248), glycosylated envelope protein (U.S. Pat. No. 4,725,669), and envelope peptides (U.S. Pat. No. 4,957,737). However, for human use, there is yet to be demonstrated a safe and effective vaccine against HIV (Sabin, 1992, Proc. Natl. Acad. Sci. USA 89:8852–8855; Hilleman, 1992, AIDS Res. Hum. Retroviruses 8:1743–1747; Ada et al. 1992, Nature 359:572; and Desrosiers, 1992, AIDS Res. Hum. Retroviruses 8:411–421). A new approach, proposing the development of a simpler retroviral vaccine against HIV, is based on the general observation that mammalian immune systems are much more successful in controlling infection caused by simpler retroviruses, as opposed to infections by more complex retroviruses such as HIV (Temin, 1993, Proc. Natl. Acad. Sci. USA 90:4419–4420). Thus, the development of a simplified HIV may result in a virus limited in replication such that an infected human may be able to respond by successfully mounting a protective response which would also be effective against wild type HIV. "Simplified" means that this engineered virus would express only the gag, pol, and env proteins. However, an obstacle to the development of such a HIV vaccine is that env production and viral replication is dependent on the presence of rev.

2. SUMMARY OF THE INVENTION

Accordingly, one object of the present invention is to provide a mechanism by which env can be produced independent of rev, so that in vitro drug screening assays will be able to distinguish between compounds acting to inhibit processes involving env, from compounds affecting rev activity.

Another object of the present invention is to provide a mechanism by which gag or gag-pol can be produced independent of rev, so that in vitro drug screening assays will be able to distinguish between compounds acting to inhibit processes involving gag or gag-pol, from compounds affecting rev activity.

Another object of the present invention is to aid the expression of cellular genes whose mRNA is either differentially spliced, alternatively spliced, incompletely spliced, or unspliced.

A further object of the present invention is to provide a mechanism where the development of a viral vaccine, requiring env and/or gag/pol production and viral replication, against HIV is independent of rev production.

A further object of the present invention is to provide a safe antigen, incapable of causing accidental infection, to be used for the detection of a humoral or cell-mediated response against HIV.

An additional object of the present invention is to provide a method for identifying and mapping other transport enhancers from cellular or viral DNA which function like the enhancer of the present invention in facilitating nuclear transport of mRNA which is either differentially spliced, alternatively spliced, incompletely spliced, or unspliced.

3. BRIEF DESCRIPTION OF THE FIGURES

FIG. 1 is a diagram showing the relevant structural differences pSVSX-5'βG and pSVSX-5'βG-MPMV, wherein pSVSX-5'βG-MPMV contains MPMV sequences (bp 8007–8557) in place of the rabbit β-globin sequences as contained in pSVSX-5'βG.

FIG. 2 is a Western blot comparison of HIV envelope protein expression in CMT3 cells transfected with either pSVSX-5'βG and pSVSX-5'βG-MPMV, in the presence (pCMVrev) or absence of rev. The structure of the relevant parts of these plasmids is shown. The headings above each lane indicate whether the env-producing plasmid was transfected alone (−) or together with pCMVrev (+).

FIG. 3 is a Northern blot analysis of polyA+RNA where:

FIG. 3A is total polyA+RNA extracted from CMT3 cells transfected with pSVSX-5'-βG or pSVSX-5'-βG-MPMV and either pCMVrev supplying a functional rev protein, or pCMVrev- that expresses a truncated, non-functional rev protein. The upper blots were probed with a 5' end-labelled oligonucleotide specific for env and the second exon of rev. The lower blots were probed with a 5' end-labelled oligonucleotide specific for mRNAs produced from pCMVrev and pCMVrev-.

Figure 4:
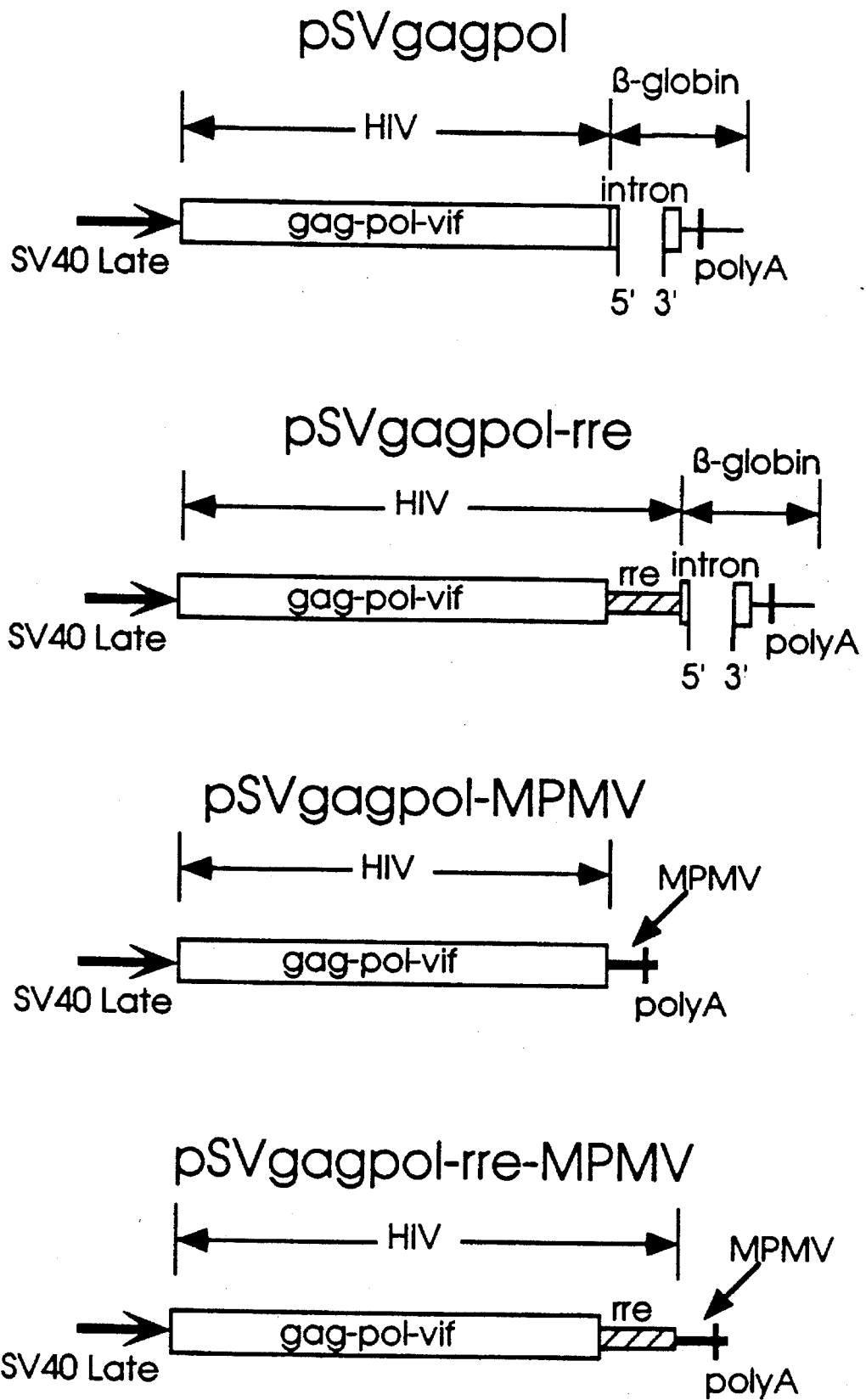
FIG. 4 is a diagram of the relevant portion of the various gag-pol expression plasmids: pSVgagpol; pSVgagpol-rre; pSVgagpol-MPMV; and pSVgagpol-rre-MPMV.
Figure 5:
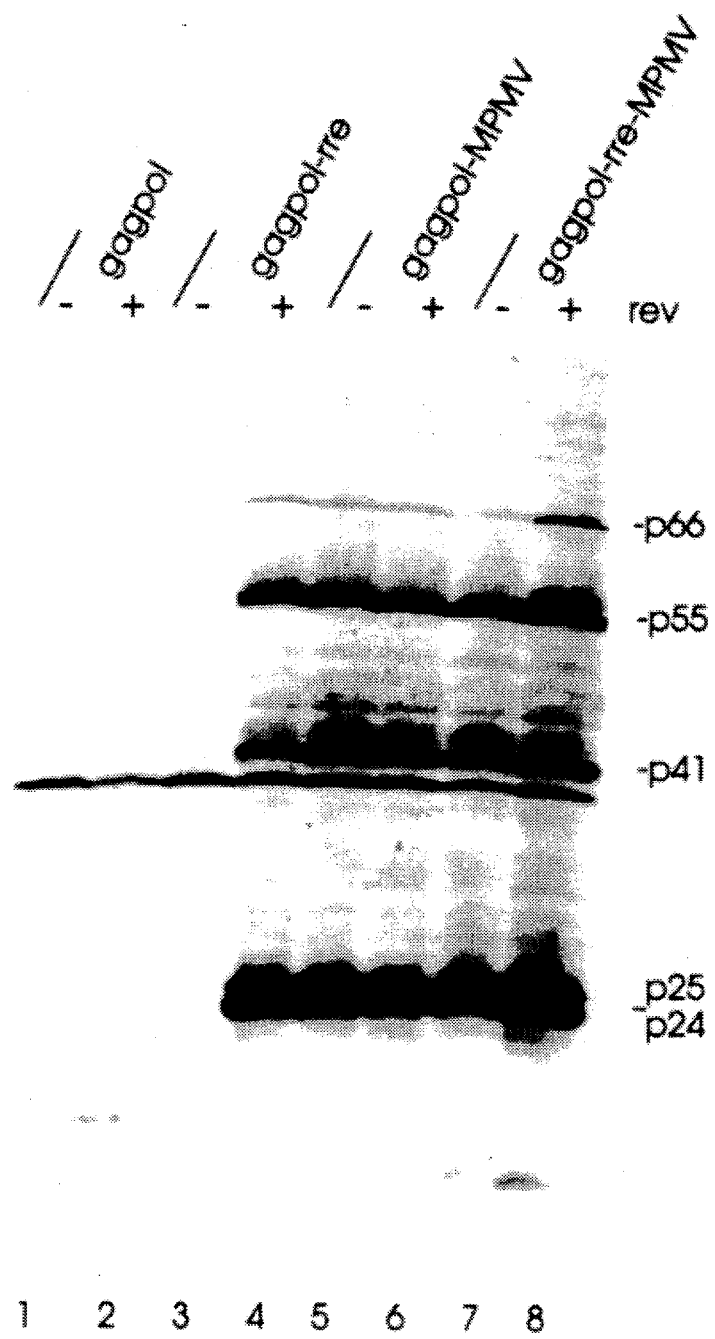

FIG. 5 is a Western blot comparing gag/pol expression in CMT3 cells from the various gag-pol expression plasmids shown in FIG. 4, in the presence (pCMVrev) or absence of rev. The headings above each lane indicate whether the gagpol plasmid was transfected alone (−) or together with pCMVrev (+). The blot was developed with pooled anti-sera from several HIV+ individuals and a rabbit anti-human antibody conjugated to alkaline phosphatase. The position of each gag-pol cleavage product on the blot is indicated.

FIG. 6 are bargraphs that represent the effect of a trans-dominant (TD) rev protein on p24 expression from plasmids containing MPMV sequences. The respective gagpol expression plasmid was transfected with 2, 5 or 10 μg of either a plasmid expressing a TD rev protein (pCMV-TD rev) or its parent vector (pCMV).

FIG. 6A represents the effect on p24 expression in 2 X10⁵ CMT3 cells previously transfected with 0.5 μg pSVgagpol-rre and pCMVrev.

FIG. 6B represents the effect on p24 expression in 2 X10⁵ CMT3 cells previously transfected with 0.5 μg pSVgagpol-MPMV.

FIG. 6C represents the effect on p24 expression in 2 X10⁵ CMT3 cells previously transfected with 0.5 μg pSVgagpol-rre-MPMV.

Figure 7:
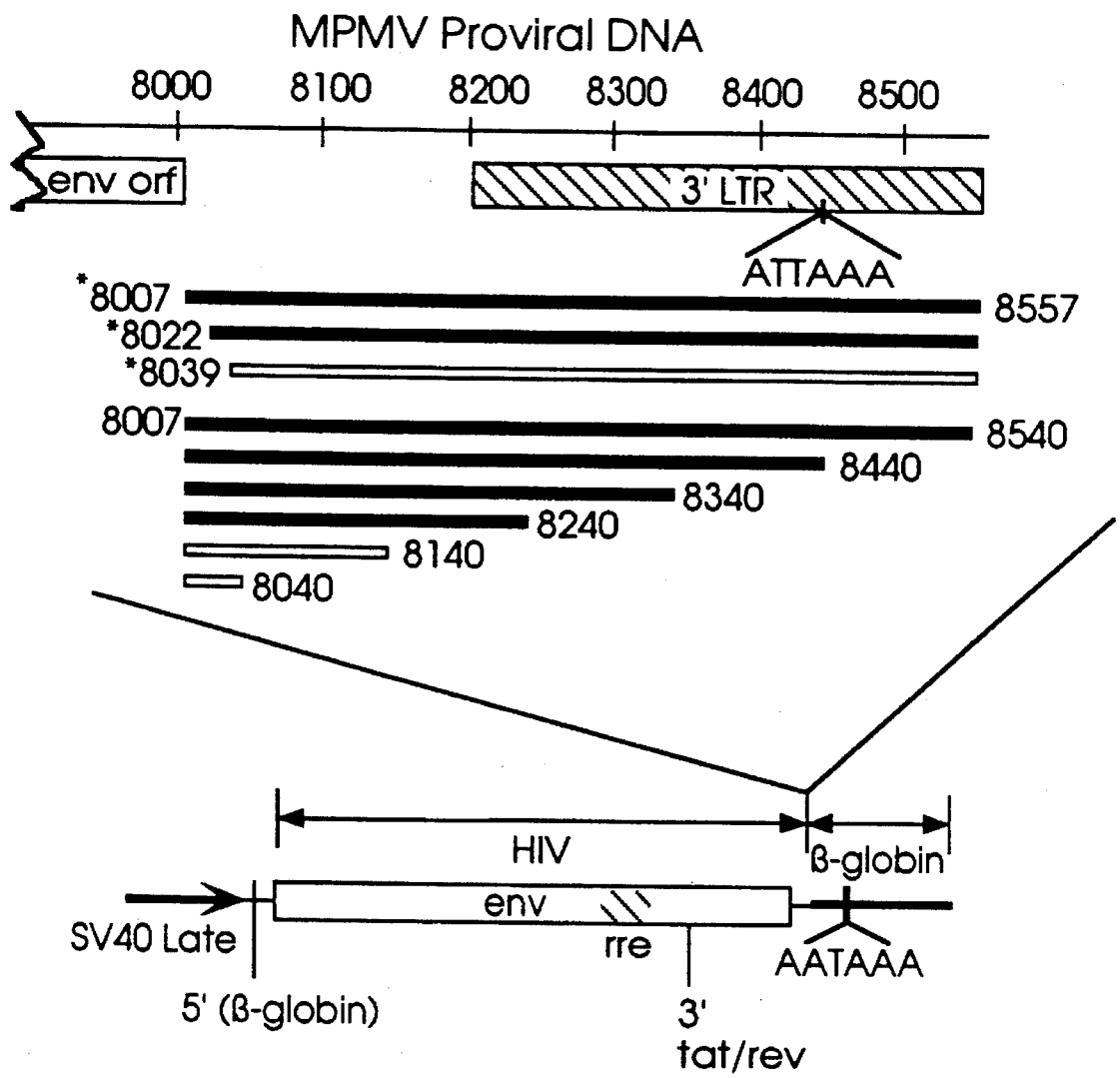

FIG. 7 is a schematic representation of the 3' end of the MPMV proviral genome. This region includes part of the env ORF, as well as the 3'LTR with its putative polyadenylation signal (ATTAAA) at bp 8438–8443. The bars immediately below the 3' end of the MPMV genome diagram indicate the various MPMV fragments, from 5' and 3' end deletion mapping of the MPMV enhancer to determine the minimal size necessary for rev-independent expression of env, that were tested for their ability to promote env expression. Fragments marked with an (*) were tested in a plasmid which lacked its own polyadenylation signal. Those without an (*) were cloned into a plasmid containing the β-globin polyadenylation signal. The open bars indicate fragments which failed to promote env expression.

FIG. 8 are Western blots of env proteins produced in CMT3 cells transfected with the vectors produced as depicted in FIG. 7, either alone or together with pCMVrev. Only the portion of each blot containing the gp160 and gp120 bands is shown. The headings above each lane show the nucleotide numbers of the MPMV sequences present in each plasmid and whether they were transfected alone (−) or together with pCMVrev (+).

Figure 8A:
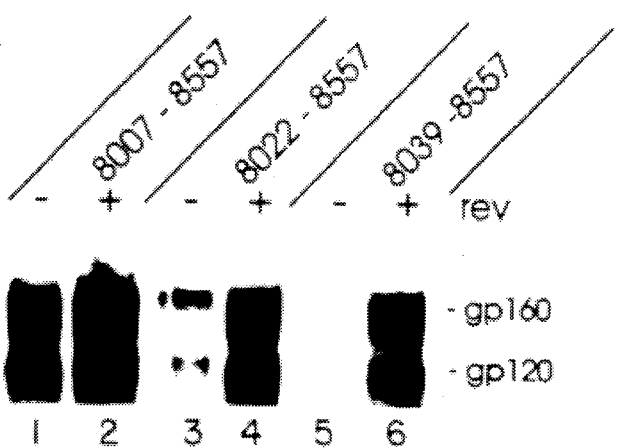

FIG. 8A is a Western blot showing the results of the 5' mapping of the functional MPMV enhancer.

Figure 8B:

FIG. 8B is a Western blot showing the results of the 3' mapping of the functional MPMV enhancer.

Figure 9:
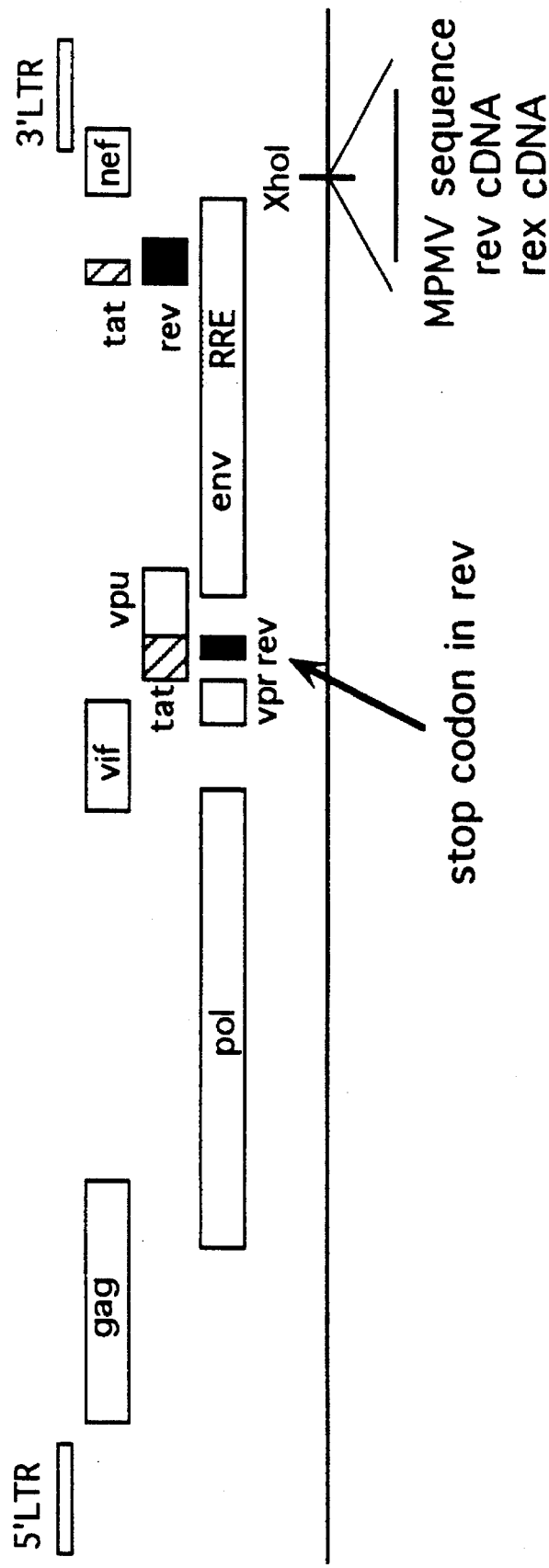

FIG. 9 is a schematic representation of the different HIV proviral constructs used to transfect HeLa cells.

Figure 10:
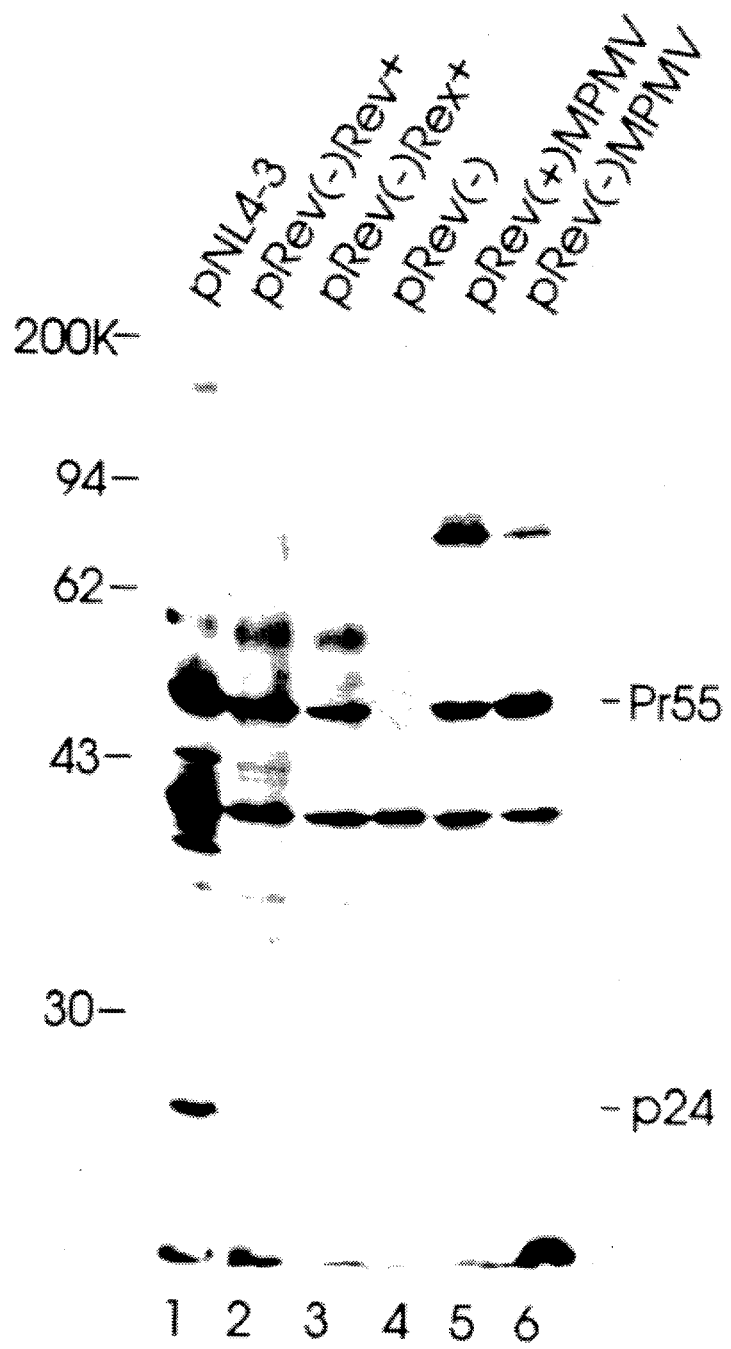

FIG. 10 is a Western blot of HIV-specific proteins expressed in HeLa cells transfected with the indicated proviral constructs pNL4-3; pRev(−)Rev⁺; pRev(−)Rex⁺; pRev(−); pRev(+)MPMV; pRev(−) MPMV.

FIG. 11 are graphs depicting replication studies, performed in MT4 cells infected with medium from the transfected HeLa cells analyzed in FIG. 10. Viral growth was measured as supernatant reverse transcriptase activity.

Figure 11A:
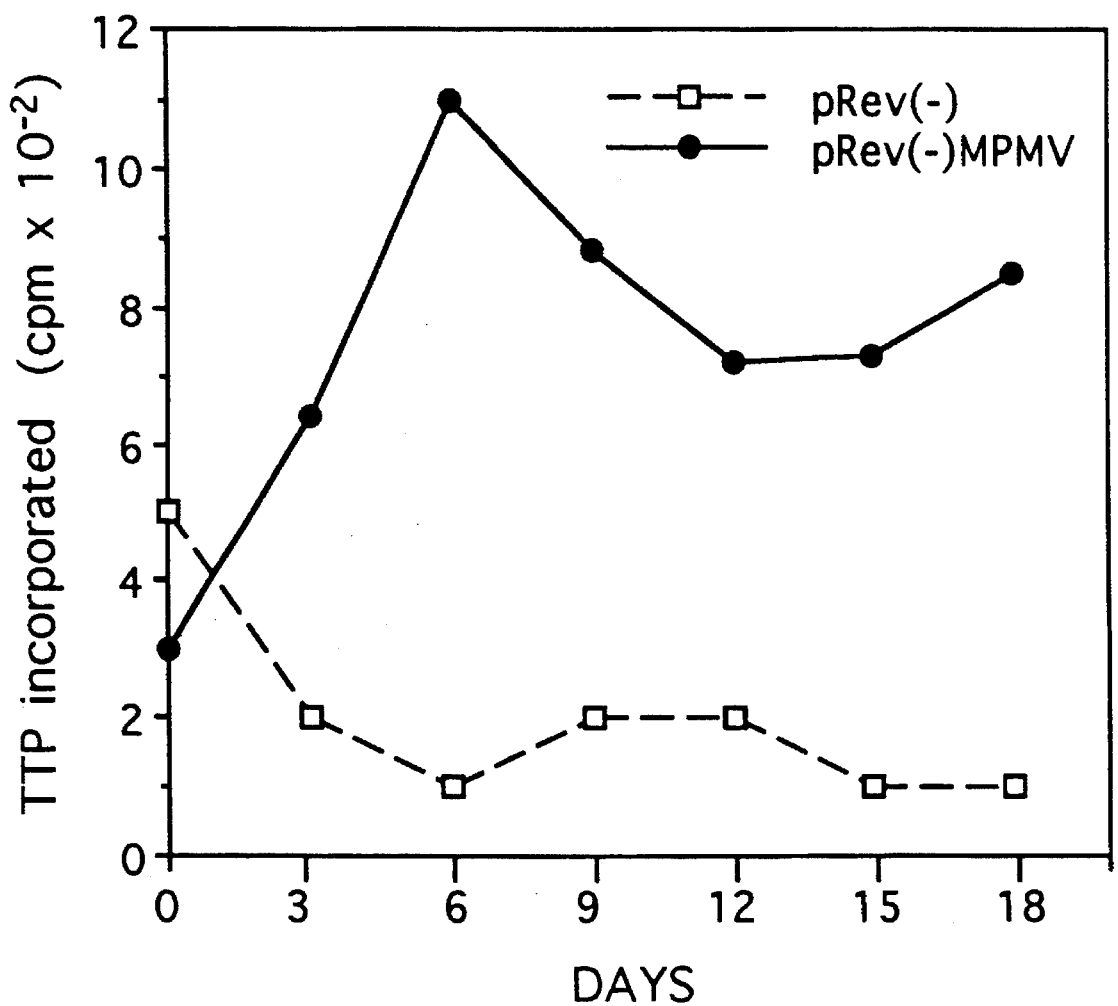

FIG. 11A represents the replication studies using medium from HeLa cells transfected with pRev(−) or pRev(−)MPMV.

Figure 11B:
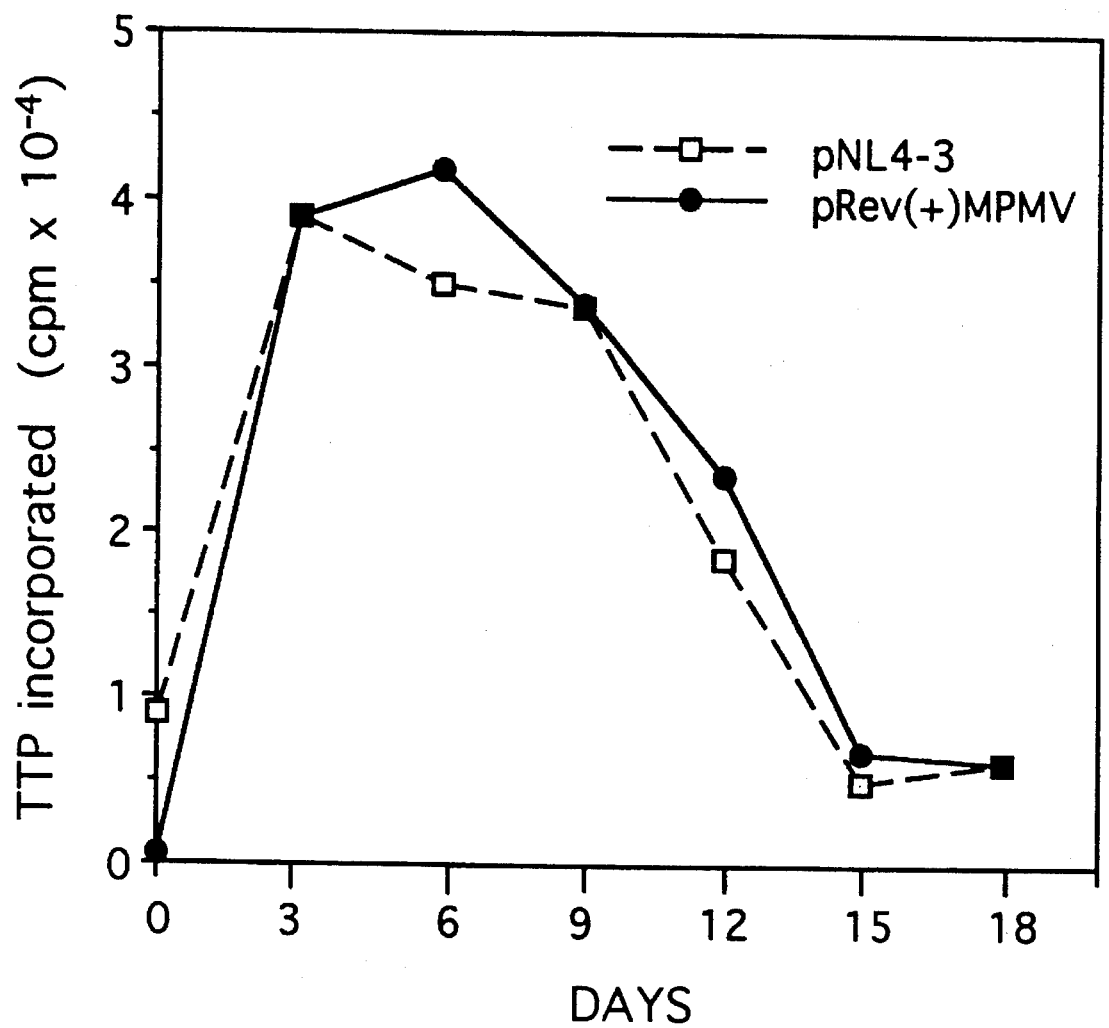

FIG. 11B represents the replication studies using medium from HeLa cells transfected with pNL4-3 or pRev(+)MPMV.

4. DETAILED DESCRIPTION OF THE INVENTION

HIV replication has been shown to be absolutely dependent on expression of the viral rev protein. This protein acts in concert with the cis-acting Rev Responsive element (RRE) present in intron containing RNAs to facilitate nuclear export of these RNAS. The present invention comprises a novel cis-acting 219 nucleotide sequence from an unrelated "simple" retrovirus, Mason Pfizer Monkey Virus (MPMV) (Sonigo et al., 1986, Cell 45: 375–385), a type D Retrovirus, that is capable of efficiently substituting for rev and the RRE in promoting the transport of intron containing HIV mRNA. More particularly, an analysis of HIV env mRNA containing the MPMV enhancer shows that the RNA was efficiently transported to the cytoplasm even in the absence of rev. Thus, the MPMV enhancer appears to overcome the normal restriction for nuclear export of this RNA. Since this genetic enhancer appears to be functionally equivalent to the RRE, but acts constitutively to transport unspliced RNA from the nucleus to the cytoplasm, we have named it the Constitutive Transport Enhancer (CTE).

Using the CTE, a variant rev-negative proviral clone of HIV has been generated which replicates with an attenuated phenotype in tissue culture cells. Also the genetic enhancer of the present invention can substitute for rev and the RRE in expression of HIV structural proteins from subgenomic constructs. The sequence comprising the genetic enhancer of the present invention is present in an untranslated region near the 3' end of the MPMV genome. More particularly, the sequence comprising the CTE which is necessary for rev-independent HIV expression maps between MPMV nucleotides 8022 and 8240 (nucleotide numbering as used in Genbank file SIVMPCG). It seems likely that this genetic enhancer allows MPMV to tap into a constitutive cellular pathway, by interacting with a cellular factor that plays a role in mRNA transport analogous to that of the rev protein, that is normally used for the transport of cellular mRNA from the nucleus to the cytoplasm. The existence of a cellular pathway for the export of incompletely spliced RNAs would imply that rev was developed, not to solve the export problem per se, but to allow HIV to exert control over the export process. Such control would ensure that the incompletely spliced RNAs are retained in the nucleus early in the replication process, before enough rev has been produced. This may help the virus avoid cytopathic effects that might ensue if the structural proteins were produced at this stage. Later, the presence of rev may make the transport of the intron containing RNAs more efficient than the constitutive machinery would allow, enabling the virus to express a large amount of the structural proteins. If rev works to perturb a cellular process in this way, the post-transcriptional role of rev seems analogous to the transcriptional role of a second HIV protein, tat. Compared to the "simpler" retroviruses such as MPMV, which use only constitutive cellular processes for transcription and transport, tat and rev provide HIV with an additional level of control. The inclusion of these regulatory genes in the HIV genome is likely to be key to the capacity of the virus to cause an infection, in which a large number of virus particles are produced and the cell is eventually killed.

Using standard techniques known to those skilled in the art of molecular biology, the CTE can be used in rev-negative proviral clones or subgenomic constructs that are utilized in the process of screening for anti-viral compounds that selectively interfere with HIV infection and replication. Hereinafter, rev-negative refers to a construct or clone in which rev function, i.e. rev-mediated transport of mRNA, is deficient. Such clones or constructs may lack either rev and/or the RRE, or may have a non-functional rev and/or RRE such as caused by deletions or mutagenesis.

In one embodiment of the present invention, the screening process would involve the use of a rev-independent expression system utilizing the CTE. If the process involves screening for a drug affecting envelope expression, gag or gag-pol expression, viral replication, or envelope function in mediating fusion, then the subgenomic construct or proviral clone used in the assay would be engineered to contain the CTE, and not to express rev. In one aspect of this embodiment, the HIV protein(s) would be expressed from an HIV promoter such as the LTR. A preferred embodiment are subgenomic constructs which express HIV proteins from other than HIV promoters. For instance, efficient envelope protein expression and tat expression has been described from a single simian virus 40 (SV40) late replacement vector containing a fragment of HIV proviral DNA (Hammarskjöld et al., 1989, supra; Rekosh et al., 1988, Proc. Natl. Acad. Sci. USA 85:334–338). Levels of expression from env were shown to be very high in this system due to the strong SV40 late promoter and amplification of the vector by replication. Although tat was produced by the vector, it has little effect on expression from env since the target region of tat (LTR) was not present. Gag and pol have also been efficiently produced using a similar SV40 based vector (Smith et al., 1990, J. Virol. 64:2743–2750). Other promoters that can be used to express HIV structural proteins in drug screening assays include the RSV promoter, the CMV immediate early promoter, and the SV40 early promoter.

Thus, where expression of HIV proteins is rev-independent, and in the case of viral particles produced in the process are the measure of drug activity, a drug that prevents or inhibits viral replication indicates activity against a viral protein/process other than involving rev. Using a subgenomic construct, constructed using promoters of the type described above, from which env production or function is the measure of drug activity, a drug that inhibits env production or fusion would be indicative of activity against env. In the cases where either gag or gag-pol production or function from the subgenomic construct is the measure of drug activity, a drug that inhibits gag or gag-pol production or function would be indicative of activity against gag or gag-pol, respectively. Similarly, drugs may be screened for rev activity using a process preferably involving parallel assays. In one assay, comprised of a subgenomic clone or proviral clone that is rev-dependent, the drug is screened for antiviral activity. In a parallel assay, comprised of a subgenomic clone or proviral clone that is rev-independent, the same drug is screened for antiviral activity. When the drug shows antiviral activity in the first assay, but not the latter, it may be concluded that the drug affects rev directly and/or rev function.

It was recently suggested that a simplified version of HIV containing only gag, pol and env might provide a safe and effective vaccine against HIV disease if it could be made to replicate in a rev-independent manner (Temin, 1993, supra). The CTE comprising the present invention may be exploited in the development of such a vaccine. In that respect, it is demonstrated herein that the CTE can be used to generate a variant rev-negative proviral clone of HIV which replicates with an attenuated phenotype in tissue culture cells.

Diagnostic assays for screening for, or diagnosing individuals that have been exposed to HIV, or evaluating their immune response against HIV, are important. In that regard, one embodiment of the present invention is to use the cells expressing HIV protein(s) by the rev-independent system described herein as a source of antigen in diagnostic assays to detect and analyze an individual's humoral and/or cell-mediated response to that respective protein. Alternately, the recombinant proteins may be purified from the expression system using methods known in the art for HIV protein purification, and the purified proteins may then be used as antigens in the diagnostic assays. Additionally, a simplified HIV may be produced using the methods of the present invention, wherein the simplified HIV may be used as a source of antigen for diagnostic assays.

A more complete appreciation of the invention, and its many attendant advantages thereof, may become apparent by referring to the following examples, in connection with the accompanying figures. These examples are provided to aid in the understanding of the features of the invention, and are not to be construed as limiting.

EXAMPLE 1

Construction of Vectors Used in Demonstrating Rev-Independent Expression pSVSX-5'βG: The plasmid pSVSX-5'βG contains an insertion of 24 bp from the region surrounding the 5' splice site from the second rabbit β-globin intron, positioned 24 nucleotides before the start of env. It was constructed similarly to p24/wtSD previously described by Lu et al (1990, Proc. Natl. Acad. Sci. USA 87:7598–7602), except that oligonucleotides containing the β-globin site were used in place of the oligonucleotides which contained the tat/rev 5' splice site.

pSVSX-5'βG-MPMV: To create pSVSX-5'βG-MPMV, a SfiI-XhoI fragment, containing the SV40 late promoter, the 5' β-globin splice site, and all of the HIV sequences, was removed from pSVSX-5'βG and recloned into pSRHS which contained the MPMV sequences. pSVSX-5'βG and pSVSX-5'βG-MPMV contain the same SV40 sequences (SV40 bp 2533–294) that include the entire early region, the origin of replication, the enhancer, the late promoter and late RNA start sites up to the KpnI site at nucleotides 294. They also contain identical HIV sequences (bp 6198 to 8896) derived from the BH10 clone. The HIV sequences are described in terms of the standard reference genome numbering system (HIVHXB2, Genbank accession number K03455). The plasmid sequences containing the ampillicin resistance gene and a bacterial origin of replication are pML2, the previously described derivative of pBR322 (Lusky and Botchan, 1981, Nature 293:79–81) in pSVSX-5'βG, and pSP72 (Promega Corp.) in pSVSX- 5'βG-MPMV.

pCMVrev; pCMVrev⁻, & pCMV-TDrev: The plasmid used to express a functional rev protein was pCMVrev. It was previously known as pRev1 and its construction has been described by Smith et al. (1990, supra).

pCMVrev⁻ was created from this plasmid by cleavage with BamHI at a unique site within the rev coding region followed by T4 DNA polymerase repair and religation. pCMVrev⁻ expresses a truncated non-functional protein.

pCMV-TDrev expresses a transdominant negative rev protein and was constructed by deletion of the codons for aa 78–79 of the rev protein in pCMVrev using site-directed mutagenesis by overlap extension using the polymerase chain reaction (Ho et al., 1989, Gene 77:51–59).

pSVgagpol; pSVgagpol-rre; pSVgagpol-MPMV; & pSVgagpol-rre-MPMV: pSVgagpol and pSVgagpol-rre have been previously described (Smith et al, 1990, supra) and differ from each other only by the presence of an 854 bp fragment, containing the RRE (HIV bp 7620–8474), in pSVgagpol-rre. pSVgagpol-MPMV and pSVgagpol-rre-MPMV were derived from these plasmids and contain MPMV sequences (bp 8007–8557) in place of the β-globin sequences. The numbering system used for the MPMV sequences are those of the 6A clone which are present in the Genbank sequence file SIVMPCG (accession number M12349). The numbering system differs from that in the publication describing this sequence (Sonigo et al, 1986, supra) due to an additional incomplete LTR between bp 416 and 743 which was deleted in the published version. To create pSVgagpol-MPMV and pSVgagpol-rre-MPMV, SfiI-BamHI fragments, containing the SV40 late promoter and all of the HIV sequences, were removed from pSVgagpol and pSVgagpol-rre, respectively and recloned into similar SV40 late replacement plasmids which contained the MPMV sequences. The MPMV derivatives contained the same SV40 sequences as their parent plasmids (SV40 bp 2533–294). These sequences include the entire early region, the origin of replication, the enhancer, the late promoter and late RNA start sites up to the KpnI site at nucleotides 294. They also contain identical HIV sequences (bp 679–5785 for pSVgagpol and bp 679–5785 followed by bp 7620–8474 for pSVgagpol-rre). These sequences were derived from the BH10 clone although the numbering system is in terms of the standard reference genome (HIVHXB2, Genbank accession number K03455). The bacterial sequences in these plasmids include an ampillicin resistance gene and a bacterial origin of replication (from pML2) (Lusky and Botchan, 1981, supra), for the plasmids lacking the MPMV enhancer, and pSP72 (Promega Corp.) for the plasmids containing it.

EXAMPLE 2

Rev-independent HIV Env Expression

Many studies have shown that expression of HIV env proteins, from plasmids containing subgenomic fragments of the HIV genome, is generally dependent on the presence of the rev-responsive element (RRE) in the env RNA and an active rev protein (Jeang et al., 1991, AIDS 5:S3–S14). One such construct is pSVSX-5'βG (see FIG. 1) (Hammarskjöld et al., 1991, pp. 345–353 in The Genetic Structure and Regulation of HIV, eds. Haseltine and Wong-Staal, Raven Press). This plasmid contains the HIV env region inserted downstream of the SV40 late promoter and upstream of rabbit β-globin sequences which provide an intron and a poly A addition signal. The plasmid also contains a β-globin 5' splice site positioned just upstream of the env gene that has been shown to be essential for env expression and rev regulation (Lu et al., 1990, supra). In contrast, removal of the downstream β-globin intron has no effect on env production or rev-regulation in this system. pSVSX-5'βG is capable of expressing large amounts of HIV env proteins in transfected cells, but expression is completely dependent on the presence of the rev protein.

Thus it was surprising to find that env expression from a similar SV40 based construct, pSRHSΔSX, appeared to be rev independent. This plasmid was similar to pSVSX-5'βG except that it lacked the upstream β-globin 5' splice site and contained sequences from the 3' end of the MPMV genome (bp 8007–8557) in place of the β-globin intron and poly A site downstream of env (see FIG. 1). The MPMV sequences in this plasmid included the 3' untranslated region downstream of the env ORF as well as the entire 3'LTR.

To investigate the basis of this observation, the β-globin sequences downstream of env in pSVSX-5'βG were replaced by the MPMV sequences to yield the plasmid pSVSX-5'βG-MPMV in accordance with Example 1 (see also FIG. 1). Then the env producing constructs pSVSX-5'βG and pSVSX-5' βG-MPMV were transfected into monkey CMT3 cells in the presence or absence of pCMVrev, which supplies rev protein. CMT3 cells (Gerard and Gluzman, 1985, Mol. Cell Biol. 5:3231–3240) were maintained in Iscove's medium supplemented with 10% calf serum. These cells are derived from the CV-1 cell line and express SV40 T-antigen under the control of the metallothionein promoter. CMT3 cells were transfected using a modification of the DEAE-dextran method as previously described (Hammarskjöld et al., 1986, Gene 43:41–50).

The cells were harvested 65 hours post-transfection and lysates of the cells were analyzed on a Western blot using an HIV env-specific serum. Procedures for Western blotting have been previously described (Hammarskjöld et al., 1986 supra; and Hammarskjöld et al, 1989, supra). The blots containing HIV env proteins were developed with a rabbit antiserum directed against gp120 and a goat anti-rabbit antibody conjugated with alkaline phosphatase. The rabbit antiserum was produced by immunization using a fragment of gp120 (amino acids 343 to 512) produced in E. coli.

Figure 2:
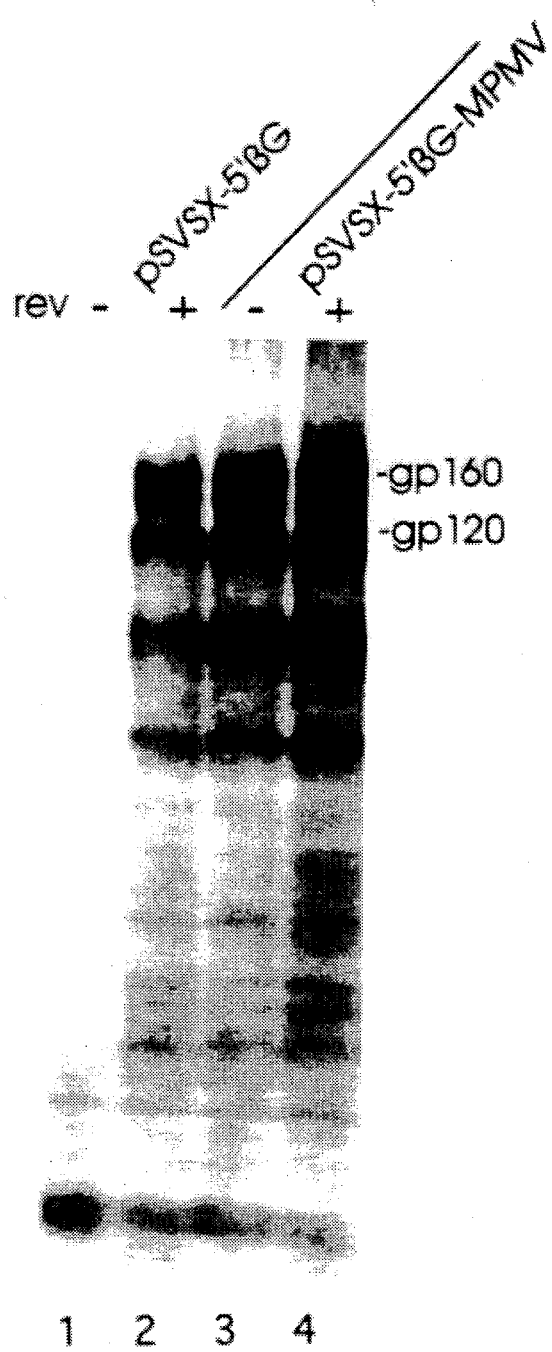

The Western blots showing the rev-dependence or rev-independence of env production in CMT3 cells transfected with env encoding constructs pSVSX-5'βG and pSVSX-5'βG-MPMV are depicted in FIG. 2. Whereas pSVSX-5'βG produced no detectable gp 160 or gp 120 proteins in the absence of rev (FIG. 2, lane 1), large amounts of these proteins were expressed from pSVSX-5'-βG-MPMV, whether or not rev was provided (FIG. 2, lane 3, rev$^-$; lane 4, rev$^+$). In fact, the amount of env protein produced from pSVSX-5' βG-MPMV, in the absence of rev (FIG. 2, lane 3), was slightly higher than that produced from pSVSX-5'βG in the presence of rev (FIG. 2 lane 2). A comparison of lanes 3 and 4 in FIG. 2 demonstrates that env expression from pSVSX-5'βG-MPMV was slightly increased when rev was provided.

To test if the observed rev-independence of pSVSX-5'βG-MPMV was specific to monkey cells, similar experiments as the ones described above were also performed in human cells (HeLa and Chang liver cells; HeLa cells being transfected using CaPO$_4$). The results clearly showed that the MPMV enhancer also promoted rev-independent env expression in these cells, although the levels of env proteins produced were lower, due to low levels of replication of the plasmids.

EXAMPLE 3

Analysis of RNA Containing the MPMV Enhancer, CTE

To further investigate expression from pSVSX-5'βG-MPMV, the HIV-specific mRNA was examined in cells co-transfected with pSVSX-5'-βG-MPMV or pSVSX-5'-βG, and either pCMVrev or a derivative of this plasmid, pCMVrev$^-$ that produces an inactive rev protein. Total and cytoplasmic RNA was extracted from transfected cells and a Northern blot analysis was performed (as previously described by Hammarskjöld et al, 1989, supra) using an oligonucleotide probe complementary to the second coding exon of rev (FIG. 3, upper panels).

Figure 3A:
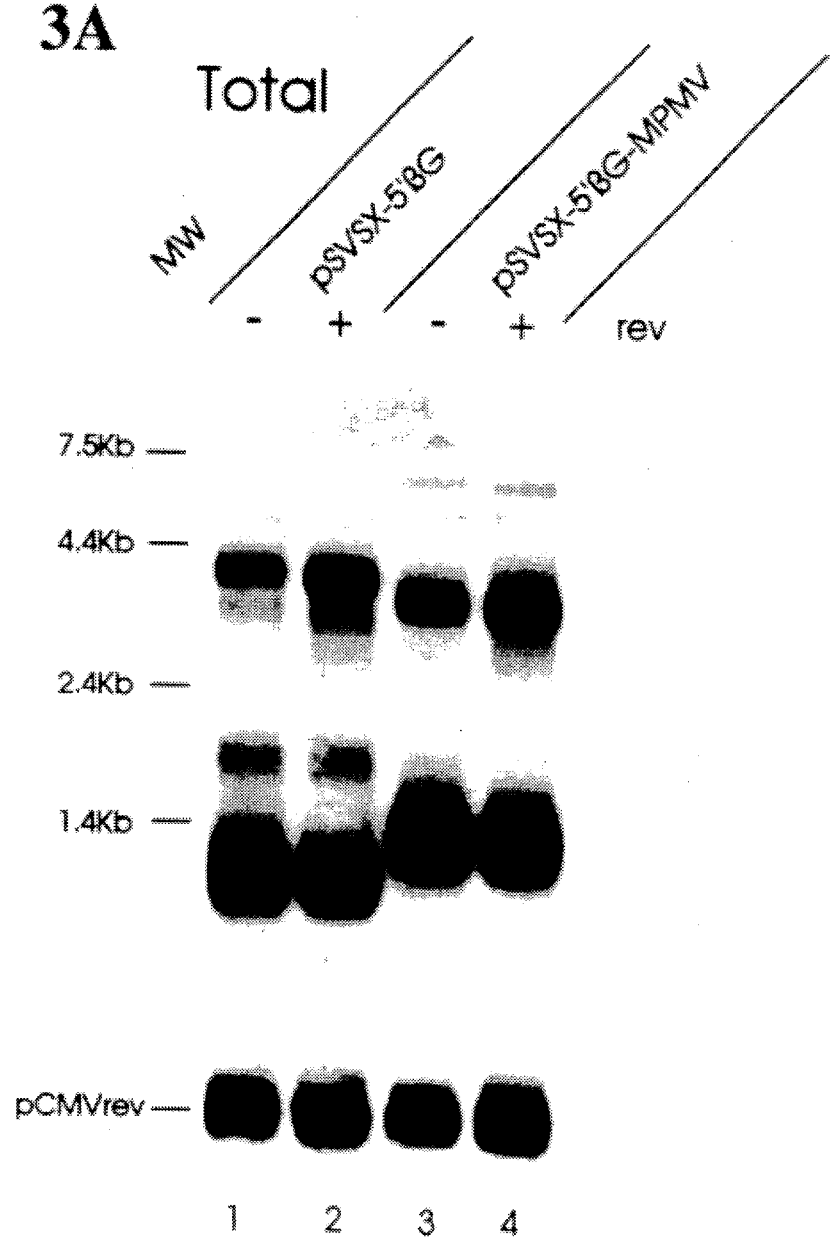
FIG. 3B is a Northern blot of cytoplasmic polyA+RNA extracted from CMT3 cells transfected with pSVSX-5'-βG or pSVSX-5'-βG-MPMV and either pCMVrev or pCMVrev-, and probed as described for FIG. 3A. The position of commercial size markers are shown.

Examination of the RNA from total cell extracts revealed that two major species of HIV-specific RNA were expressed in cells transfected with either pSVSX- 5'βG (FIG. 3A, upper panel, lanes 1, rev$^-$, & 2, rev$^+$) or pSVSX-5'βG-MPMV (FIG. 3A, upper panel, lanes 3, rev$^-$, & 4, rev$^+$). The overall pattern of expression was the same with or without a functional rev protein, although in both cases, somewhat higher levels of the larger species was observed when rev was supplied. For pSVSX-5'βG (FIG. 3 lanes 1 & 2) the larger RNA was about 4 kb in size and the smaller RNA was about 1 kb. For pSVSX-5'βG-MPMV (FIG. 3, lanes 3 & 4)

the RNAs were 3.6 kb and 1.4 kb in size. In both cases, the larger RNA was shown to be totally unspliced, whereas the smaller RNA was spliced. In cells transfected with pSVSX-5'βG, this RNA was doubly spliced, and lacked the downstream β-globin intron, as well as the intron between the β-globin 5' splice site and the "tat/rev" 3' splice site (see FIG. 1). In the case of pSVSX-5' βG-MPMV, the smaller species was singly spliced and lacked the intron between the 5'β-globin and 3' tat/rev splice sites. Thus, for each plasmid only the larger RNA was capable of expressing the envelope proteins.

Figure 3B:
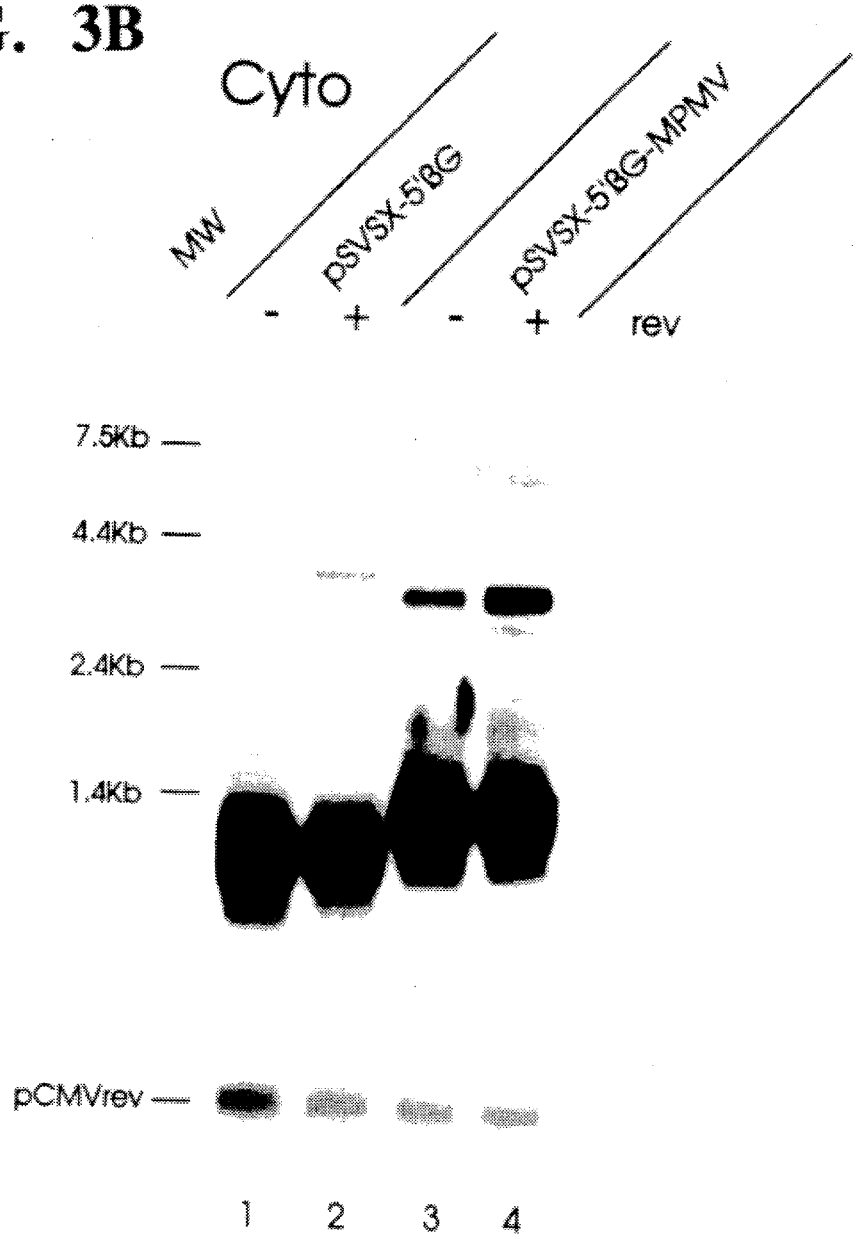

In contrast to the results with total RNA preparations, analysis of cytoplasmic RNA showed major differences in expression between the two plasmids (FIG. 3B, upper panel). Although the same two species of RNA as in total RNA were observed for each plasmid in the presence of a functional rev (FIG. 3B, lanes 2 & 4), no unspliced RNA was seen with pSVSX-5'βG when rev was lacking (FIG. 3B, lane 1). This was consistent with our previous results and showed that export of the unspliced env RNA from the nucleus to the cytoplasm was absolutely dependent on rev. In contrast, a considerable amount of unspliced env RNA was present in the cytoplasm in cells transfected with pSVSX-5'βG-MPMV, with (FIG. 3B, lane 4) or without (FIG. 3B, lane 3) rev. The level of this RNA was higher in cytoplasmic extracts from cells transfected with pSVSX-5'βG-MPMV in the absence of rev (FIG. 3B, lane 3), than in cytoplasmic extracts from cells transfected with pSVSX-5'βG in the presence of rev (FIG. 3B, lane 2). Extracts from cells transfected with both rev and pSVSX-5'βG-MPMV contained even more of this species of RNA (FIG. 3, lane 4). These results correlated well with the results of the protein analysis (see FIG. 1, lanes 2, 3 and 4) and indicated that the presence of MPMV sequences in the plasmid overcame the need for rev in transport of the unspliced RNA from the nucleus to the cytoplasm. The quantitative differences seen with or without rev also suggested that rev was still able to either stabilize the RNA or act in concert with the CTE to accomplish export of the env RNA from the nucleus.

As a control for possible variation in transfection efficiency and loading, the Northern blots were stripped and reprobed with an oligonucleotide specific for the mRNAs produced from the plasmids expressing the wild type and mutant rev. The observed levels of these RNAs were similar in each total and cytoplasmic lane (FIG. 3 A and B, lower panels).

Similar results were obtained when the MPMV sequences were inserted into a plasmid containing the β-globin intron showing that the presence or absence of this intron had no effect on the rev-independent phenotype.

EXAMPLE 4

Rev-independent Gag and Gag-pol Expression

In HIV infected cells, rev and the RRE are necessary not only for expression of the env proteins, but also for expression of the proteins derived from the gag and pol open reading frames (Jeang et al, 1991, supra). In a previous study, it was shown that this requirement was maintained when the gag/pol/vif region of the HIV genome was inserted into an SV40 late replacement vector (Smith et al., 1990, supra). Expression of the gag and gag-pol proteins from this vector required the RRE in cis, as well as the rev protein in trans. In the presence of rev and the RRE, this plasmid was capable of expressing virus like particles, which were efficiently released into the medium of transfected cells.

In order to test if the MPMV sequences could also substitute for rev and the RRE in this context, the β-globin sequences in the pSVgagpol and pSVgagpol-rre were exchanged for the MPMV sequences (see Example 1). A diagram depicting the structure of the original plasmids and the MPMV-containing derivatives is shown in FIG. 4. The expression of the gag and gag-pol proteins from plasmids pSVgagpol, pSVgagpol-rre, pSVgagpol-MPMV, and pSVgagpol-rre-MMPV were analyzed in a transient transfection experiment with and without a pCMVrev that supplied rev. The results of this experiment are shown in the Western blots depicted in FIG. 5, with the blots for HIV gag and pol proteins being developed with serum from an HIV positive patient and a goat anti-human antibody conjugated with alkaline phosphatase.

As before, the expression of the gag and gag-pol proteins from the plasmids containing the beta globin sequences was completely dependent on both rev and the RRE. Thus no expression of these proteins was detected from pSVgagpol with (FIG. 5, lane 2) or without (FIG. 5, lane 1) rev, whereas large amounts of the gag and gag-pol proteins were expressed from pSVgagpol-rre, but only when rev was present (FIG. 5, lane 3, rev⁻; and lane 4, rev⁺). In contrast, these proteins were efficiently expressed from both pSVgagpol-MPMV and pSVgagpol-rre-MPMV whether or not rev was present (FIG. 5, lanes 5–8). Since the RRE was not present in pSVgagpol-MPMV, these experiments showed that the MPMV sequences abolished the need for rev and did not require the presence of the RRE to promote expression.

Cells transfected with pSVgagpol-rre-MPMV contained larger amounts of the gag-pol proteins in the presence of rev (FIG. 5, lane 8) compared to the levels of these proteins in its absence (FIG. 5, lane 7). This was analogous to the result obtained with the env expression plasmid (as shown in FIG. 3B, lanes 2 & 3). In contrast, rev did not increase the levels of expression from pSVgag-pol-MPMV. This showed that rev could still promote additional expression from the plasmid containing the MPMV sequences, but, as expected, only when the RRE was present.

EXAMPLE 5

A Transdominant Negative Rev Protein does not Affect HIV Expression in Constructs Containing the MPMV Enhancer It has been shown that rev function can be inhibited through the expression of transdominant-negative mutant rev proteins (Jeang et al, 1991, supra). One of these mutant rev proteins, M10, is mutated in the proposed effector domain (Malim et al., 1989, Cell 58:205–214). The M10 protein has been shown to bind to the RRE (Malim and Cullen, 1991 Cell 65:241–248), but it is unable to promote transport of RNA from the nucleus to the cytoplasm. The basis for the negative transdominance of this protein is still unclear. It has been suggested that the protein may work by binding to the RRE and blocking the binding of a cellular factor, or alternatively, the protein may bind a limiting cellular factor necessary for rev function (squelching). It was therefore of interest to determine whether a transdominant rev protein, similar to M10, could have an inhibitory effect on expression from the plasmids that were producing gag-pol through the pathway mediated by the MPMV sequences.

To do this, the two MPMV sequence containing constructs, pSVgagpol-MPMV and pSVgagpol-rre-MPMV, were transfected separately into CMT3 cells together with increasing amounts of pCMV-TDrev, a plasmid expressing a transdominant rev protein that carried a 2 amino acid deletion in the rev effector domain (see Example 1). As a control for possible inhibitory effects of the co-transfection itself, cells were also co-transfected with the MPMV sequence containing constructs and increasing amounts of pCMV, the parent of pCMV-TDrev, which did not contain a rev insert. To demonstrate that the transdominant protein was functional, another control experiment was performed, in which cells were triply transfected with the rev-dependent pSVgag-pol-RRE, pCMVrev and increasing amounts of pCMV-TDrev. Gag and gag-pol expression was assessed using an ELISA assay, which measured p24 that was released into the medium of the transfected cells. The media from the transfected cells was harvested and assayed for p24 antigen as previously described (Smith et al, 1990, supra). The relative amount of p24 produced for each amount of pCMV-TDrev was calculated by dividing the amount of p24 produced in the transfections with pCMV-TDrev by the amount of p24 produced in the transfections with pCMV. This was done to normalize for possible inhibitory effects of the increasing amounts of CMV plasmid. The amount of p24 produced without pCMV-TDrev was set at 1.0. The results were normalized at each concentration of plasmid to take into account any inhibitory effects seen from the co-transfection.

The determination of whether a transdominant rev protein, from pCMV-TDrev, could have an inhibitory effect on expression from the plasmids that were producing gag-pol through the pathway mediated by the MPMV sequences, is illustrated in FIG. 6A, B, & C. FIG. 6 shows that the transdominant rev protein had no significant effect on expression from either pSVgagpol-MPMV (FIG. 6A) or pSVgagpol-rre-MPMV (FIG. 6B). In contrast, FIG. 6C shows that for pSVgagpol-rre, as expected, p24 levels were dramatically reduced (90% inhibition) with 2 μg of pCMV-TDrev and were non detectable when higher amounts of pCMV-TDrev were used. Thus the transdominant rev protein was able to completely inhibit rev function, but did not interfere with the function of the MPMV enhancer, even when both the RRE and the MPMV sequences were present in the same plasmid.

EXAMPLE 6

The MPMV Sequences Contain a Cis-acting Enhancer that Works Only in the Correct Orientation The sequences of the MPMV genome that were shown to substitute for rev and the RRE in the experiments described above in Examples 2-5, included the complete 3'LTR as well as the region between the env ORF and the LTR (see FIG. 7). An inspection of these sequences did not reveal any open reading frame which seemed large enough to encode a protein. It thus appeared likely that the MPMV sequence exerted its effect as a cis-acting enhancer. To test this directly, an experiment was performed to determine if the rev-independent, envelope protein producing plasmid, pSVSX-5'βG-MPMV, could promote expression of gag and gag-pol proteins from pSVgagpol-rre without added rev. Analysis of the products produced from co-transfections of these plasmids, with or without added rev, showed that gag or gag-pol products were not made unless rev was also present. As expected, envelope proteins were produced with or without added rev. In addition, a plasmid was constructed that was analogous to pSVSX-5'βG-MPMV except that the MPMV sequences were inserted in the opposite orientation. Results of transfection assays showed that env production from these plasmids were rev-dependent. Taken together, these results showed that the MPMV sequences had to be present in cis and in the correct orientation, in order to obtain rev-independent expression. Thus, the sequences appear to work as an RNA enhancer which facilitate nuclear transport of mRNA such as that transcribed from env, gag, pol, vif, vpr, and vpu.

EXAMPLE 8

Mapping the Minimal Cis-acting Enhancer, the CTE

To further map the enhancer necessary for rev-independent expression, deletions were made from the 5'end of the MPMV fragment in pSVSX-5'βG-MPMV and the resulting constructs were analyzed for envelope protein expression. To map the 5'end of the enhancer, pSVSX-5'βG-MPMV was cleaved with XhoI and treated briefly with Bal 31 exonuclease. The DNA was then repaired with T4 DNA polymerase and recircularized. To determine the extent of the deletions in the resulting plasmids, the region surrounding the original XhoI site was sequenced.

The resultant constructs, containing the deletions for mapping the cis-acting enhancer, were used to transfect cells and the transfected cells were subsequently analyzed for envelope protein expression by Western blot analysis. This analysis showed that removal of the sequences between bp 8007–8022 still allowed rev-independent env expression (FIG. 8A, lanes 1 and 3), while further deletion to bp 8039 completely abrogated the rev-independent response (FIG. 8A, lane 5). Thus, the 5' end of the enhancer mapped to between bp 8022 and 8039.

To map the 3' end of the enhancer, MPMV sequences were positioned between an XhoI site present at the end of the HIV sequences and a BglII site present within the β-globin sequences of pSVSX-5'βG (i.e. between env and the polyadenylation signal as shown in FIG. 7). This removed 726 bp from pSVSX-5'βG which included the entire β-globin intron but left the β-globin polyadenylation signal in the plasmid. The different MPMV fragments were amplified by polymerase chain reaction (PCR) using a synthetic oligonucleotide complementary to sequences 5' of the XhoI site in pSVSX-5' βG-MPMV in combination with synthetic oligonucleotides complementary to different sequences within the MPMV sequences. These oligos contained a 5' overhang designed to create a BamHI site after amplication. After purification and restriction enzyme cleavage of the PCR-amplified products, the resultant fragments were cloned into pSVSX-5'βG cleaved with XhoI and BamHI, as illustrated in FIG. 7. The resultant plasmids carrying the different MPMV sequences were then transfected into CMT3 cells and analyzed for env expression in the presence or absence of rev and analyzed by Western blot analysis (FIG. 8B).

As expected, all of the constructs were able to express env proteins in the presence of rev. In the absence of rev, only the two constructs containing the shortest MPMV fragments (8007–8040 and 8007–8140) failed to produce any detectable env proteins (FIG. 8B, lanes 9 and 11). These results clearly demonstrated that the MPMV polyadenylation signal was not necessary for the rev-independent phenotype and mapped the 3' end of the cis-acting enhancer to a point somewhere between bp 8140 and 8240. Similar mapping experiments were also performed using either pSVgagpol-rre or pSVSX-5'βG as the recipient plasmids. In these experiments, the two smaller fragments were again the only ones that failed to give rev-independent expression.

Taken together the results of these experiments mapped the sequence that is necessary for the rev-independent phenotype to an enhancer of 219 bp situated between MPMV nucleotides 8022 and 8240 (SEQ ID NO:1). On the 5' side, it is clear that the sequence does not include the env ORF, which stops at nucleotide 8002, and that the end point of the enhancer lies between nucleotides 8022 and 8039. On the 3' side, the end point lies between nucleotides 8140 and 8240. Since the 3'LTR begins at bp 8205, the enhancer has been found to be present within the intragenic region between the end of the env ORF and the 3'LTR. Subsequent mapping experiments have identified the enhancer to be situated between MPMV nucleotides 8022–8175 (SEQ ID NO:2).

The defined sequence comprising the CTE does not share any obvious sequence homology with the RRE's of HIV-1 or HIV-2 or the RxRE's of HTLV-I or HTLV-II. However, it has 93 and 84% homology with regions, presumed to be functionally equivalent, from the Simian SRV-1 and Simian SRV-2 type D retroviruses (Power et al., 1986, Science 231:1567–1572; Thayer et al., 1987, Virology 157:317–329). This is compared to a homology within the LTRs of 88% for MPMV and SRV-1, and 70% for MPMV and SRV-2. Thus, the high level of conservation seen in the CTE region appears to be significant and strongly suggests that the sequence has been conserved to maintain an important viral function. Interestingly, in SRV-1, the region contains an open reading frame capable of encoding a protein of 109 amino acids. The ORF is not maintained in MPMV or SRV-2 and its significance is not known. The sequence displays little homology with any other sequence present in the Genbank or EMBL databases.

EXAMPLE 9

Method for Identifying and Mapping Other Transport Enhancers from Cellular or Viral DNA Using the illustrative methods and constructs according to the present invention, specifically according to Examples 1, 4, 8, and 13, other transport enhancers from cellular or viral DNA may be identified and mapped. It is apparent to those skilled in the art that cellular genes and viral genes may use transport enhancers that are the functional equivalent of the CTE of the present invention. That is, a transport enhancer may be present in cellular DNA and viral DNA; be transcribed as part of a mRNA transcript which is either differentially spliced, incompletely spliced, or unspliced; and facilitate nuclear transport of such RNA thereby facilitating expression from the cellular gene or viral gene into the respective gene product. To illustrate this embodiment, it is apparent that since all retroviruses have to carry out nuclear transport of mRNA, functional equivalents of the CTE exist. Sequences from retroviral DNA may be selected, based on such parameters as homology to the CTE or frequency of occurrence of particular sequences in mRNA transcripts. Alternatively, a library of genomic fragments can be screened for transport enhancer function.

In one illustration of this embodiment, DNA sequences may be inserted into pSVSX-5'βG according to the methods of Example 8, and as illustrated in FIG. 7 for MPMV sequences. For example, DNA sequences being screened for transport enhancers may be inserted into pSVSX-5'βG using one or more retriction sites at the end of HIV sequences and between env and the β-globin polyadenylation signal. The resultant constructs are then transfected into cells and the transfected cells are subsequently harvested and analyzed for envelope expression using methods such as those described in Examples 2 and 8. Detection of envelope protein, in the absence of rev, indicates the presence of a transport enhancer in DNA inserted into the subgenomic construct contained within the transfected cells. The transport enhancer contained within that cellular or viral DNA insert can be mapped further by deletion experiments using methods similar to those described in Example 8, and as illustrated for MPMV sequences in FIG. 7.

In another illustration of this embodiment, DNA sequences may be inserted into pSVgagpol (FIG. 4) according to the methods of Example 4. For example, DNA sequences being screened for transport enhancers may be inserted into pSVgagpol using one or more retriction sites at the end of HIV sequences and between gag-pol-vif and the β-globin polyadenylation signal. The resultant constructs are then transfected into cells and the transfected cells are subsequently harvested and analyzed for expression of HIV gag and pol proteins using methods such as those described in Example 4. Detection of gag and pol proteins, in the absence of rev, indicates the presence of a transport enhancer in the subgenomic construct contained within the transfected cells. The cellular or viral DNA inserted into the subgenomic construct which is found to contain the transport enhancer can be mapped further by deletion experiments using the similar methods described in Example 8, and as illustrated for MPMV sequences in FIG. 7.

In yet another illustration of this embodiment, DNA sequences may be inserted into pβ8F according to the methods of Example 13. For example, DNA sequences being screened for transport enhancers may be inserted into pβ8F using one or more restriction sites either in the β-globin intron or the exon downstream from this intron. The resultant constructs are then transfected into cells; the transfected cells are subsequently harvested; and cytoplasmic and total RNA is extracted and analyzed using methods such as those described in Example 13. Demonstration of transport of the unspliced intron-containing RNA from the nucleus to the cytoplasm, in the absence of rev, indicates the presence of a transport enhancer in the subgenomic construct contained within the transfected cells. The cellular or viral DNA inserted into the subgenomic construct which is found to contain the transport enhancer can be mapped further by deletion experiments using the similar methods described in Example 8, and as illustrated for MPMV sequences in FIG. 7.

Other constructs (plasmid or viral vectors) may be used to identify and map transport enhancers contained in cellular or viral DNA inserted therein. The essential elements of a such a construct are that it contain a gene or sequence that is trancribed into mRNA which is either differentially spliced, alternatively spliced, incompletely spliced or unspliced and thus not normally transported from the nucleus into the cytoplasm; and restrictions sites within the vector in which a DNA sequence, being evaluated for the presence of a transport enhacer, can be inserted into the vector such that the DNA sequence is transcribed as part of the mRNA transcript. Detection of a corresponding gene product, or of the respective mRNA which is transported from the nucleus to the cytoplasm, as according to the methods described herein, may be indicative of the presence of a transport element within the insert of cellular or viral DNA.

EXAMPLE 10

The MPMV Enhancer Allows Rev Independent HIV Replication

To investigate whether the MPMV enhancer was also able to substitute for rev in HIV replication, a fragment containing MPMV nucleotides 8007–8240 was inserted into the nef region of a rev-negative derivative of pNL4-3. pNL4-3 is an infectious proviral clone of HIV-1 (Adachi et al., 1986, J. Virol. 59:284–291). The derivative contained a mutation that created a stop codon at aa 12 in the first coding exon of rev. The MPMV- containing construct (pRev(–)MPMV) was then transfected into HeLa cells. As controls, cells were also transfected with pNL4-3 and the original rev-negative construct lacking the MPMV enhancer (pRev(–)). In addition, transfections were also performed with two other derivatives of pRev(–). One of these, pRev(–)Rex contained a cDNA copy of the HTLV-I rex gene inserted into a unique XhoI site at the start of the nef gene in pRev(–). The HTLV rex protein has previously been shown to substitute for rev in HIV expression and replication (Rimsky et al, 1988, supra; Lewis et al, 1990, supra). The other derivative, pRev(–)Rev+, contained a cDNA copy of the HIV rev gene inserted into the XhoI site of nef. These plasmids are schematically depicted in FIG. 9.

The HeLa cells were harvested 48 hours after transfection with the different constructs and extracts were subjected to Western blot analysis using a serum from an HIV positive individual (FIG. 10). As expected, several HIV specific proteins were expressed in cells transfected with pNL4-3 (FIG. 10, lane 1). The Pr55 and p24 proteins, as well as several intermediate proteolytic products, were readily detected in extracts of these cells. None of these proteins were expressed in cells transfected with pRev(–) (FIG. 10, lane 4), confirming previous studies which showed that rev is absolutely necessary for structural protein expression. In contrast, HIV-specific proteins were observed in extracts of cells transfected with pRev(–)MPMV (FIG. 10, lane 6); or pRev(–)Rev+ (FIG. 10, lane 2); or pRev(–)Rex (FIG. 10, lane 3); or pRev(+)MPMV (FIG. 10, lane 5). An additional polypeptide with an apparent molecular weight of about 85 kD was detected in the cells transfected with pRev(+)MPMV and pRev(–)MPMV (FIG. 10, lanes 5 and 6). The identity of this protein is unknown.

To analyze whether the MPMV containing constructs were able to replicate in human CD4+ cells, the medium from the cells transfected with pNL4-3, pRev(–), pRev(–)MPMV and pRev(+)MPMV, respectively, was used to infect MT4 cells. MT4 cells, a CD4+ human T-cell line, were maintained in RPMI medium with 10% fetal calf serum. Supernatant medium from transfected HeLa cells were mixed with $10^6$ MT4 cells. The infected cultures were maintained for 18 days. Two-fifths of the medium and cells were removed every 3 days after infection and replaced with the same amount of fresh medium. To measure virus replication, the removed medium was analyzed for virion-associated reverse transcriptase activity, as described previously (Willey et al., 1988, J. Virol. 62:139–147).

FIG. 11A and B show replication curves in infected MT4 cells during the 18 day period. As expected, no replication was detected in cells infected with the medium from cells transfected with pRev(–) (FIG. 11A, -●-). In contrast, a significant amount of replication was observed in cells infected with the medium from the cells transfected with pRev(–)MPMV (FIG. 11A, --□--). However, the replication of pRev(–)MPMV was significantly impaired compared to that of pNL4-3 (FIG. 11B, --□--), indicating that pRev(–)MPMV represents an attenuated virus. In contrast, the pRev(+)MPMV virus (FIG. 11B, -●-) seemed to replicate as efficiently as pNL4-3. Thus, the CTE allows replication of a rev-negative proviral clone.

Described herein according to this embodiment, are the basic elements for producing a replicating rev-negative proviral clone using the CTE. Such a proviral clone, as illustrated by pRev(–) MPMV, can result in an attenuated virus that is a simplified version of HIV having potential as a safe and effective vaccine against HIV disease (Temin, 1993, supra). Thus, the composition comprising the vaccine would contain as the vaccine antigen a prophylactically-effective amount of the attenuated virus made according to the present invention. Alternatively, the vaccine may contain DNA comprising one or more subgenomic constructs for rev-independently expressing HIV protein, as according to the present invention. Methods for vaccination with DNA have been described previously (Fynan et al., 1993, Proc. Natl. Acad. Sci. USA 90:11478–11482, herein incorporated by reference).

EXAMPLE 11

Rev-Independent Expression In Drug Screening Assays

According to Examples 1–8, and 10, a small enhancer from MPMV can substitute for rev and the RRE in expression of HIV structural proteins from subgenomic constructs. This enhancer also allows replication of a rev-negative proviral clone. An analysis of HIV env mRNA containing the MPMV enhancer showed that the RNA was efficiently transported to the cytoplasm even in the absence of rev. Thus, the MPMV enhancer appears to overcome the normal restriction for nuclear export of this RNA.

Using standard techniques known to those skilled in the art of molecular biology, the CTE can be used in rev-negative proviral clones or subgenomic constructs that are utilized in the process of screening for anti-viral compounds that selectively interfere with HIV infection and replication. Essentially, the basic elements of different embodiments of a rev-independent drug screening assay using the CTE have been described herein. In one embodiment, subgenomic constructs which efficiently express HIV env protein, from other than an HIV promoter and independent of rev, has been described and illustrated according to Examples 1 and 2 (pSVSX-5'βG-MPMV). Further, transfection of the cells, in which the subgenomic constructs express env, has also been described. Thus, it would be obvious to one skilled in the art, with the disclosure of the present invention, and with pSVSX-5'βG-MPMV or a functionally equivalent recombinant vector containing the CTE, to develop a rev-independent screening assay directed to identifying drugs that affect env expression or function. Numerous cells have been used for HIV protein expression including, but not limited to, Cos, Hela, CV-1, 293 cells and CHO cells. One skilled in the art would appreciate that depending on the promoter and the origin of replication of the expression vector used, that some cells may be better suited for expression from and replication of that recombinant vector. Thus, the relative amount of env produced in such an expression system in the presence of the agent being screened for anti-viral activity, can be compared to the relative amount of env produced in the absence of the same agent to determine anti-viral activity. Similarly, in a fusion assay system, the relative amounts of env production, and env function in mediating fusion can be compared from an assay run in the presence of the agent, and in an assay run in the absence of the agent.

Similarly, gag and pol have also been efficiently produced from subgenomic constructs, from other than an HIV promoter and independent of rev, as illustrated according to Examples 1 and 4 (pSVgagpol-MPMV). Further, transfection of the cells, in which the subgenomic constructs express gag and pol, has also been described. Thus, it would be obvious to one skilled in the art, with the disclosure of the present invention, and with pSVgagpol-MPMV or a functionally equivalent recombinant vector containing the CTE, to develop a rev-independent screening assay directed to identifying drugs that affect gag and/or pol expression by comparing the relative amounts of the respective protein in the presence of the agent as compared to the relative amounts in the absence of the agent.

EXAMPLE 12

The Use of the CTE to Aid in Gene Expression of Genes Whose m-RNA is Differentially Spliced It has been demonstrated by the foregoing examples that the sequence comprising the CTE appears to function as a genetic enhancer which, when fused proximally to a gene encoding a HIV protein in a location just 3' to the gene and in a cis orientation, can result in rev-independent HIV expression. Although the actual mechanism of action has yet to be confirmed, it seems likely that this genetic enhancer allows MPMV to tap into a constitutive cellular pathway, by interacting with a cellular factor that plays a role in mRNA transport analogous to that of the rev protein, that is normally used for the transport of cellular mRNA from the nucleus to the cytoplasm. For genes whose mRNA is differentially spliced, or unspliced (ex., from cDNA) and using standard techniques known to those skilled in the art of molecular biology, the CTE can be incorporated into a recombinant vector to aid in the expression of the gene by providing a mechanism for nuclear transport of the mRNA transcribed from the gene wherein the enhancer is part of the transcript.

EXAMPLE 13

The Use of the CTE in an Intron or Exon Position to Achieve Nuclear Export of Unspliced Cellular m-RNA It has previously been shown that intron containing cellular RNA is generally only exported from the nucleus following removal of all complete introns by splicing (Chang et al., 1989, supra; Legrain et al., 1989, supra). In one study it was shown that intron-containing betaglobin RNA was exported from the nucleus if the HIV RRE was present in the RNA and the rev protein was provided in the cells (Chang et al., 1989, supra). To analyze whether the MPMV CTE could be utilized for transport of intron containing betaglobin RNA, the plasmid pβ8F was obtained from Dr. Phillip Sharp. This plasmid was one of the constructs used in the Chang et al. study, and contains an RRE within the betaglobin intron. From pβ8F was expressed unspliced intron containing RNA that accumulates in the nucleus. An MPMV fragment containing the MPMV CTE (MPMV nt#8007–8340) was inserted into pβ8F either in the betaglobin intron (resulting in plasmid pβ8F (MPMV) intron) or in the exon downstream of this intron (resulting in plasmid pβ8F (MPMV) exon).

Separately, pβ8F (MPMV) intron and pβ8F (MPMV) exon were transfected into CMT3 cells either in cotransfections with a plasmid expressing the HIV rev protein (pCMV rev) or with the plasmid pCMVrev- which expressed an inactive form of the rev protein. As a control, cells were also transfected with the original plasmid pβ8F and pCMVrev or pCMVrev-. Cells were harvested 48 hours post transfection, and cytoplasmic and total RNA was extracted. The RNA expressed from the plasmids was analyzed by Northern blot analysis using betaglobin-specific probes. Quantitation of the RNA was performed using auto-radiography followed by scanning with a Laser Densitometer. For each transfection, the values obtained were corrected for transfection efficiency using the signal obtained from the pCMVrev or pCMVrev- plasmid as a normalization factor.

The results of these experiments are summarized in Table 1. The values for total and cytoplasmic RNA are relative values, setting the value obtained in the sample that was cotransfected with a functional rev as 1.0 in each case.

TABLE 1

| Plasmid | Rev | Total RNA | Cyto. RNA |
|---|---|---|---|
| pβ8F | − | 0.8 | 0.1 |
| pβ8F | + | 1.0 | 1.0 |
| Pβ8F (MPMV) exon | − | 0.6 | 1.1 |
| pβ8F (MPMV) exon | + | 1.0 | 1.0 |
| pβ8F (MPMV) intron | − | 1.0 | 0.8 |
| pβ8F (MPMV) intron | + | 1.0 | 1.0 |

These results show that insertion of the MPMV CTE enables transport of the unspliced intron-containing RNA from the nucleus to the cytoplasm without the need for a functional rev protein. This is true whether the CTE is present in an intron or an exon position. This is in contrast to the results with pβ8F which show that rev is required for transport and the appearance of the cytoplasmic RNA. Thus, these results indicate that the CTE can be used as a general tool to achieve nuclear export of unspliced, incompletely and/or alternatively spliced RNAs.

EXAMPLE 14

Diagnostic Assays Utilizing HIV Proteins or Virus Produced by Rev-independent Expression This embodiment of the present invention is to provide HIV antigens, i.e. particularly compositions containing env and/or gag/pol produced from the rev-independent expression system of the present invention, for evaluating the immune response of an individual exposed to HIV. The compositions containing HIV antigen may comprise cells transfected with a construct containing one or more genes encoding HIV protein, and a transport enhancer which facilitates the nuclear transport of the mRNA transcribed from the gene(s); the purified HIV protein therefrom; or a simplified HIV made according to Example 10.

For example, when considering diagnostic assays to measure or detect a humoral response, and if the composition comprised cells transfected with pSVSX-5'βG-MPMV, those transfected cells may serve as a source of antigen because some of the env protein will be incorporated into the cell membranes of the transfected cells, thereby being accessible to antibody. Alternatively, the gene product such as env, can be purified from cell lysates or cell media using methods known in the art such as immunoaffinity chromatography. The transfected cells; purified HIV protein derived therefrom; or simplified HIV may be used as antigen in a variety of diagnostic tests for the detection of HIV antibody in human serum or in other biological fluids. Such immunodiagnostic assays include, but are not limited to, radioimmunoassay, enzyme-linked immunosorbent assay (ELISA), "sandwich" assay, precipitin reaction, agglutination assay, fluorescent immunoassay, and chemiluminescence-based immunoassay. The basic element of the immunoassay is that the antigen forms a complex with HIV-specific antibody, and the antigen-antibody complex is then detected in the immunodiagnostic assay.

The cell-mediated response, or the lack thereof, is thought to be important in the development of HIV infection. One mode of therapy, which is being evaluated for its potential to inhibit HIV infection, is the use of certain agents to restore an infected individual's deficient cell-mediated response against the virus. There are several methods known in the art for evaluating cell-mediated immunity. One such method, cytotoxicity assays, measure the capability of cytotoxic T-lymphocytes to kill target cells. The cells of the present invention, i.e. cells expressing HIV env and/or gag/pol using the transport enhancer of the present invention, may serve as the target cells in a cytotoxicity assay. More particularly, the cells rev-independently expressing HIV protein would be grown in the presence of a label. A "label" means a detectable marker which is incorporated inside the target cell, which is released with the internal cell components upon lysis of the cell, and thereby becomes detectable in the surrounding reaction mixture containing the cell lysate. The label can be selected from either radioactive or non-radioactive markers, with an example of a typical label being $^{51}Cr$. Alternatively, an HIV protein that is produced, and remains primarily in the transfected cell, may serve as the marker in lieu of a "label".

In an illustration of this embodiment, T-lymphocytes would be isolated from blood drawn from an HIV-infected individual. The purified T-lymphocytes would be mixed in a reaction with the target cells containing the label $^{51}C$ internally. If the individual has cytotoxic T-lymphocytes that are specifically immunized against antigens contained on the HIV proteins expressed by the target cell, the lymphocytes will interact directly with the target cells causing cell-mediated cytolysis of the target cells. The surrounding reaction mixture can then be quantitatively assayed for $^{51}Cr$ release from the labeled target cells. Thus, the cells rev-independently expressing HIV protein may be used in evaluating the cell-mediated immunity against HIV in an HIV-infected individual either before or after therapeutic attempts at immunomodulation of the cell-mediated response.

EXAMPLE 15

According to Examples 1–8, and 10, a small enhancer from MPMV can substitute for rev and the RRE in expression of HIV structural proteins from subgenomic constructs. This enhancer also allows replication of a rev-negative proviral clone. An analysis of HIV env mRNA containing the MPMV enhancer showed that the RNA was efficiently transported to the cytoplasm even in the absence of rev. Thus, the MPMV enhancer appears to overcome the normal restriction for nuclear export of this RNA.

As is known in the art, other complex retroviruses have evolved a mechanism similar to HIV to facilitate the nuclear transport of intron-containing RNA. HTLV-I and HTLV-II utilize a protein called rex, whereas the simian immunodeficiency virus (SIV) utilizes a functionally similar transacting protein. Using standard techniques known to those skilled in the art of molecular biology, and in accordance with the embodiments of the illustrative examples of the present invention, the CTE can be used in proviral clones or subgenomic constructs of other complex retroviruses, wherein the respective transacting protein is either lacking or non-functional and/or it's respective responsive element is lacking or non-functional. Thus, the CTE can allow for cytoplasmic expression of complex retroviral intron-containing RNA which is otherwise dependent on a transacting protein similar in function to HIV rev.

Although the present invention has been described in some detail by way of illustration and example for purposes of clarity and understanding, various modifications will become apparent to those skilled in the art from the foregoing description and figures. However, it will be appreciated by those of skill in the art that the techniques, constructs, and embodiments disclosed herein are preferred embodiments only, and that in general, there exists equivalent methods, constructs, and techniques that, in view of the disclosure, may be employed to achieve the same result. For example, although most of the subgenomic constructs contained a promoter other than the LTR which drove expression of HIV proteins, it is apparent to one skilled in the art that the HIV LTR could also be used as the promoter. Additionally, MPMV is a type D retrovirus isolate. The CTE of MPMV has 93% homology and 84% homology with equivalent regions from the simian SRV-1 and SRV-2 type D retrovirus isolates, respectively. This and other evidence suggests that isolates of type D retroviruses have a genetic enhancer that is the functional equivalent of the CTE of MPMV. Thus, from the disclosure of the present invention, these functional equivalents can be identified and isolated. Furthermore, since all retroviruses must transport unspliced RNA from the cell nucleus to cytoplasm, it is apparent that functionally equivalent transport enhancers exist in retroviruses other than type D. There need not be sequence identity between the various transport enhancers to have functional equivalence. Such modifications are intended to be included within the spirit of this application and within the scope of the appended claims.

We claim:

1. A purified sub-genomic nucleic acid molecule encoding a cis-acting retroviral, mRNA constitutive transport enhancer element comprising the nucleotide sequence of SEQ ID NO:2, or an analogous nucleic acid molecule obtained from simian retrovirus type 1 (SRV-1) or simian retrovirus type 2 (SRV-2), wherein said nucleic acid molecule enhances the nuclear to cytoplasmic transport of a heterologous m-RNA transcript when present in said transcript.

2. The nucleic acid molecule of claim 1, wherein said heterologous mRNA transcript is a rev-dependent HIV transcript containing RNA sequences for at least one gene selected from the group consisting of env, gag, pol, vif, vpr, and vpu, and said nuclear to cytoplasmic transport occurs in the absence of Rev expression.

3. A recombinant, attenuated, rev-deficient proviral human immunodeficiency virus clone containing the cis-acting retroviral constitutive transport enhancer element according to claim 1, wherein said transport enhancer element is present in a correct orientation and transcribed in a cell as part of a mRNA transcript of one or more HIV genes, wherein the genes are selected from the group consisting of env, gag, and pol, and wherein said attenuation results in impaired viral replication.

4. The recombinant, attenuated, rev-deficient proviral human immunodeficiency virus clone of claim 3, wherein the constitutive transport enhancer element is inserted into the nef coding region of the infectious proviral clone.

5. A purified and isolated nucleotide sequence comprising a constitutive transport enhancer wherein the nucleotide sequence consists of SEQ ID NO:2.

* * * * *